(12) United States Patent
Marquart et al.

(10) Patent No.: US 7,636,595 B2
(45) Date of Patent: Dec. 22, 2009

(54) METHOD AND APPARATUS FOR CALIBRATING NON-LINEAR INSTRUMENTS

(75) Inventors: Joel G Marquart, Pembroke Pines, FL (US); Mark W Hunter, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 602 days.

(21) Appl. No.: 10/976,328

(22) Filed: Oct. 28, 2004

(65) Prior Publication Data
US 2006/0094958 A1 May 4, 2006

(51) Int. Cl.
*A61B 5/00* (2006.01)
(52) U.S. Cl. .................. 600/424; 600/411; 600/427
(58) Field of Classification Search ............... 600/411, 600/424, 427; 606/81
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |

(Continued)

FOREIGN PATENT DOCUMENTS

CA 964149 3/1975

(Continued)

OTHER PUBLICATIONS

"Prestige Cervical Disc System Surgical Technique", 12 pgs.

(Continued)

*Primary Examiner*—Brian Casler
*Assistant Examiner*—Peter Luong
(74) *Attorney, Agent, or Firm*—Harness, Dickey

(57) ABSTRACT

A method and apparatus for performing a calibration and navigation of a member. The member may be calibrated relative to a selected portion, such as a sensor on an instrument. The calibrated member may then be navigated with a selected system. The calibration technique can be infinitely flexible and not rigid or designed for specific components. Moreover, the calibration may occur when the member is interconnected to an end of the instrument that is non-co-axial with another end of the instrument.

60 Claims, 6 Drawing Sheets

U.S. PATENT DOCUMENTS

| | | | |
|---|---|---|---|
| 4,017,858 A | 4/1977 | Kuipers | |
| 4,037,592 A | 7/1977 | Kronner | |
| 4,052,620 A | 10/1977 | Brunnett | |
| 4,054,881 A | 10/1977 | Raab | |
| 4,117,337 A | 9/1978 | Staats | |
| 4,173,228 A | 11/1979 | Van Steenwyk et al. | |
| 4,182,312 A | 1/1980 | Mushabac | |
| 4,202,349 A | 5/1980 | Jones | |
| 4,228,799 A | 10/1980 | Anichkov et al. | |
| 4,256,112 A | 3/1981 | Kopf et al. | |
| 4,262,306 A | 4/1981 | Renner | |
| 4,287,809 A | 9/1981 | Egli et al. | |
| 4,298,874 A | 11/1981 | Kuipers | |
| 4,314,251 A | 2/1982 | Raab | |
| 4,317,078 A | 2/1982 | Weed et al. | |
| 4,319,136 A | 3/1982 | Jinkins | |
| 4,328,548 A | 5/1982 | Crow et al. | |
| 4,328,813 A | 5/1982 | Ray | |
| 4,339,953 A | 7/1982 | Iwasaki | |
| 4,341,220 A | 7/1982 | Perry | |
| 4,346,384 A | 8/1982 | Raab | |
| 4,358,856 A | 11/1982 | Stivender et al. | |
| 4,368,536 A | 1/1983 | Pfeiler | |
| 4,396,885 A | 8/1983 | Constant | |
| 4,396,945 A | 8/1983 | DiMatteo et al. | |
| 4,418,422 A | 11/1983 | Richter et al. | |
| 4,419,012 A | 12/1983 | Stephenson et al. | |
| 4,422,041 A | 12/1983 | Lienau | |
| 4,431,005 A | 2/1984 | McCormick | |
| 4,485,815 A | 12/1984 | Amplatz | |
| 4,506,676 A | 3/1985 | Duska | |
| 4,543,959 A | 10/1985 | Sepponen | |
| 4,548,208 A | 10/1985 | Niemi | |
| 4,571,834 A | 2/1986 | Fraser et al. | |
| 4,572,198 A | 2/1986 | Codrington | |
| 4,583,538 A | 4/1986 | Onik et al. | |
| 4,584,577 A | 4/1986 | Temple | |
| 4,608,977 A | 9/1986 | Brown | |
| 4,613,866 A | 9/1986 | Blood | |
| 4,617,925 A | 10/1986 | Laitinen | |
| 4,618,978 A | 10/1986 | Cosman | |
| 4,621,628 A | 11/1986 | Bludermann | |
| 4,625,718 A | 12/1986 | Olerud et al. | |
| 4,638,798 A | 1/1987 | Shelden et al. | |
| 4,642,786 A | 2/1987 | Hansen | |
| 4,645,343 A | 2/1987 | Stockdale et al. | |
| 4,649,504 A | 3/1987 | Krouglicof et al. | |
| 4,651,732 A | 3/1987 | Frederick | |
| 4,653,509 A | 3/1987 | Oloff et al. | |
| 4,659,971 A | 4/1987 | Suzuki et al. | |
| 4,660,970 A | 4/1987 | Ferrano | |
| 4,673,352 A | 6/1987 | Hansen | |
| 4,688,037 A | 8/1987 | Krieg | |
| 4,701,049 A | 10/1987 | Beckmann et al. | |
| 4,705,395 A | 11/1987 | Hageniers | |
| 4,705,401 A | 11/1987 | Addleman et al. | |
| 4,706,665 A | 11/1987 | Gouda | |
| 4,709,156 A | 11/1987 | Murphy et al. | |
| 4,710,708 A | 12/1987 | Rorden et al. | |
| 4,719,419 A | 1/1988 | Dawley | |
| 4,722,056 A | 1/1988 | Roberts et al. | |
| 4,722,336 A | 2/1988 | Kim et al. | |
| 4,723,544 A | 2/1988 | Moore et al. | |
| 4,727,565 A | 2/1988 | Ericson | |
| RE32,619 E | 3/1988 | Damadian | |
| 4,733,969 A | 3/1988 | Case et al. | |
| 4,737,032 A | 4/1988 | Addleman et al. | |
| 4,737,794 A | 4/1988 | Jones | |
| 4,737,921 A | 4/1988 | Goldwasser et al. | |
| 4,742,356 A | 5/1988 | Kuipers | |
| 4,742,815 A | 5/1988 | Ninan et al. | |
| 4,743,770 A | 5/1988 | Lee | |
| 4,743,771 A | 5/1988 | Sacks et al. | |
| 4,745,290 A | 5/1988 | Frankel et al. | |
| 4,750,487 A | 6/1988 | Zanetti | |
| 4,753,528 A | 6/1988 | Hines et al. | |
| 4,761,072 A | 8/1988 | Pryor | |
| 4,764,016 A | 8/1988 | Johansson | |
| 4,771,787 A | 9/1988 | Wurster et al. | |
| 4,779,212 A | 10/1988 | Levy | |
| 4,782,239 A | 11/1988 | Hirose et al. | |
| 4,788,481 A | 11/1988 | Niwa | |
| 4,791,934 A | 12/1988 | Brunnett | |
| 4,793,355 A | 12/1988 | Crum et al. | |
| 4,794,262 A | 12/1988 | Sato et al. | |
| 4,797,907 A | 1/1989 | Anderton | |
| 4,803,976 A | 2/1989 | Frigg et al. | |
| 4,804,261 A | 2/1989 | Kirschen | |
| 4,805,615 A | 2/1989 | Carol | |
| 4,809,694 A | 3/1989 | Ferrara | |
| 4,821,200 A | 4/1989 | Öberg | |
| 4,821,206 A | 4/1989 | Arora | |
| 4,821,731 A | 4/1989 | Martinelli et al. | |
| 4,822,163 A | 4/1989 | Schmidt | |
| 4,825,091 A | 4/1989 | Breyer et al. | |
| 4,829,373 A | 5/1989 | Leberl et al. | |
| 4,836,778 A | 6/1989 | Baumrind et al. | |
| 4,838,265 A | 6/1989 | Cosman et al. | |
| 4,841,967 A | 6/1989 | Chang et al. | |
| 4,845,771 A | 7/1989 | Wislocki et al. | |
| 4,849,692 A | 7/1989 | Blood | |
| 4,860,331 A | 8/1989 | Williams et al. | |
| 4,862,893 A | 9/1989 | Martinelli | |
| 4,869,247 A | 9/1989 | Howard, III et al. | |
| 4,875,165 A | 10/1989 | Fencil et al. | |
| 4,875,478 A | 10/1989 | Chen | |
| 4,884,566 A | 12/1989 | Mountz et al. | |
| 4,889,526 A | 12/1989 | Rauscher et al. | |
| 4,896,673 A | 1/1990 | Rose et al. | |
| 4,905,698 A | 3/1990 | Strohl, Jr. et al. | |
| 4,923,459 A | 5/1990 | Nambu | |
| 4,931,056 A | 6/1990 | Ghajar et al. | |
| 4,945,305 A | 7/1990 | Blood | |
| 4,945,914 A | 8/1990 | Allen | |
| 4,951,653 A | 8/1990 | Fry et al. | |
| 4,955,891 A | 9/1990 | Carol | |
| 4,961,422 A | 10/1990 | Marchosky et al. | |
| 4,977,655 A | 12/1990 | Martinelli | |
| 4,989,608 A | 2/1991 | Ratner | |
| 4,991,579 A | 2/1991 | Allen | |
| 5,002,058 A | 3/1991 | Martinelli | |
| 5,005,592 A | 4/1991 | Cartmell | |
| 5,013,317 A | 5/1991 | Cole et al. | |
| 5,016,639 A | 5/1991 | Allen | |
| 5,017,139 A | 5/1991 | Mushabac | |
| 5,027,818 A | 7/1991 | Bova et al. | |
| 5,030,196 A | 7/1991 | Inoue | |
| 5,030,222 A | 7/1991 | Calandruccio et al. | |
| 5,031,203 A | 7/1991 | Trecha | |
| 5,042,486 A | 8/1991 | Pfeiler et al. | |
| 5,047,036 A | 9/1991 | Koutrouvelis | |
| 5,050,608 A | 9/1991 | Watanabe et al. | |
| 5,054,492 A | 10/1991 | Scribner et al. | |
| 5,057,095 A | 10/1991 | Fabian | |
| 5,059,789 A | 10/1991 | Salcudean | |
| 5,078,140 A | 1/1992 | Kwoh | |
| 5,079,699 A | 1/1992 | Tuy et al. | |
| 5,086,401 A | 2/1992 | Glassman et al. | |
| 5,094,241 A | 3/1992 | Allen | |
| 5,097,839 A | 3/1992 | Allen | |
| 5,098,426 A | 3/1992 | Sklar et al. | |
| 5,099,845 A | 3/1992 | Besz et al. | |
| 5,099,846 A | 3/1992 | Hardy | |
| 5,105,829 A | 4/1992 | Fabian et al. | |

| | | | | | |
|---|---|---|---|---|---|
| 5,107,839 A | 4/1992 | Houdek et al. | 5,353,795 A | 10/1994 | Souza et al. |
| 5,107,843 A | 4/1992 | Aarnio et al. | 5,353,800 A | 10/1994 | Pohndorf et al. |
| 5,107,862 A | 4/1992 | Fabian et al. | 5,353,807 A | 10/1994 | DeMarco |
| 5,109,194 A | 4/1992 | Cantaloube | 5,359,417 A | 10/1994 | Müller et al. |
| 5,119,817 A | 6/1992 | Allen | 5,368,030 A | 11/1994 | Zinreich et al. |
| 5,142,930 A | 9/1992 | Allen et al. | 5,371,778 A | 12/1994 | Yanof et al. |
| 5,143,076 A | 9/1992 | Hardy et al. | 5,375,596 A | 12/1994 | Twiss et al. |
| 5,152,288 A | 10/1992 | Hoenig et al. | 5,377,678 A | 1/1995 | Dumoulin et al. |
| 5,160,337 A | 11/1992 | Cosman | 5,383,454 A | 1/1995 | Bucholz |
| 5,161,536 A | 11/1992 | Vikomerson et al. | 5,385,146 A | 1/1995 | Goldreyer |
| 5,178,164 A | 1/1993 | Allen | 5,385,148 A | 1/1995 | Lesh et al. |
| 5,178,621 A | 1/1993 | Cook et al. | 5,386,828 A | 2/1995 | Owens et al. |
| 5,186,174 A | 2/1993 | Schlondorff et al. | 5,389,101 A | 2/1995 | Heilbrun et al. |
| 5,187,475 A | 2/1993 | Wagener et al. | 5,391,199 A | 2/1995 | Ben-Haim |
| 5,188,126 A | 2/1993 | Fabian et al. | 5,394,457 A | 2/1995 | Leibinger et al. |
| 5,190,059 A | 3/1993 | Fabian et al. | 5,394,875 A | 3/1995 | Lewis et al. |
| 5,193,106 A | 3/1993 | DeSena | 5,397,329 A | 3/1995 | Allen |
| 5,197,476 A | 3/1993 | Nowacki et al. | 5,398,684 A | 3/1995 | Hardy |
| 5,197,965 A | 3/1993 | Cherry et al. | 5,399,146 A | 3/1995 | Nowacki et al. |
| 5,198,768 A | 3/1993 | Keren | 5,400,384 A | 3/1995 | Fernandes et al. |
| 5,198,877 A | 3/1993 | Schulz | 5,402,801 A | 4/1995 | Taylor |
| 5,207,688 A | 5/1993 | Carol | 5,403,321 A | 4/1995 | DiMarco |
| 5,211,164 A | 5/1993 | Allen | 5,408,409 A | 4/1995 | Glassman et al. |
| 5,211,165 A | 5/1993 | Dumoulin et al. | 5,413,573 A | 5/1995 | Koivukangas |
| 5,211,176 A | 5/1993 | Ishiguro et al. | 5,417,210 A | 5/1995 | Funda et al. |
| 5,212,720 A | 5/1993 | Landi et al. | 5,419,325 A | 5/1995 | Dumoulin et al. |
| 5,214,615 A | 5/1993 | Bauer | 5,423,334 A | 6/1995 | Jordan |
| 5,219,351 A | 6/1993 | Teubner et al. | 5,425,367 A | 6/1995 | Shapiro et al. |
| 5,222,499 A | 6/1993 | Allen et al. | 5,425,382 A | 6/1995 | Golden et al. |
| 5,224,049 A | 6/1993 | Mushabac | 5,426,683 A | 6/1995 | O'Farrell, Jr. et al. |
| 5,228,442 A | 7/1993 | Imran | 5,426,687 A | 6/1995 | Goodall et al. |
| 5,230,338 A | 7/1993 | Allen et al. | 5,427,097 A | 6/1995 | Depp |
| 5,230,623 A | 7/1993 | Guthrie et al. | 5,429,132 A | 7/1995 | Guy et al. |
| 5,233,990 A | 8/1993 | Barnea | 5,433,198 A | 7/1995 | Desai |
| 5,237,996 A | 8/1993 | Waldman et al. | RE35,025 E | 8/1995 | Anderton |
| 5,249,581 A | 10/1993 | Horbal et al. | 5,437,277 A | 8/1995 | Dumoulin et al. |
| 5,251,127 A | 10/1993 | Raab | 5,443,066 A | 8/1995 | Dumoulin et al. |
| 5,251,635 A | 10/1993 | Dumoulin et al. | 5,443,489 A | 8/1995 | Ben-Haim |
| 5,253,647 A | 10/1993 | Takahashi et al. | 5,444,756 A | 8/1995 | Pai et al. |
| 5,255,680 A | 10/1993 | Darrow et al. | 5,445,144 A | 8/1995 | Wodicka et al. |
| 5,257,636 A | 11/1993 | White | 5,445,150 A | 8/1995 | Dumoulin et al. |
| 5,257,998 A | 11/1993 | Ota et al. | 5,445,166 A | 8/1995 | Taylor |
| 5,261,404 A | 11/1993 | Mick et al. | 5,446,548 A | 8/1995 | Gerig et al. |
| 5,265,610 A | 11/1993 | Darrow et al. | 5,447,154 A | 9/1995 | Cinquin et al. |
| 5,265,611 A | 11/1993 | Hoenig et al. | 5,448,610 A | 9/1995 | Yamamoto et al. |
| 5,269,759 A | 12/1993 | Hernandez et al. | 5,453,686 A | 9/1995 | Anderson |
| 5,271,400 A | 12/1993 | Dumoulin et al. | 5,456,718 A | 10/1995 | Szymaitis |
| 5,273,025 A | 12/1993 | Sakiyama et al. | 5,457,641 A | 10/1995 | Zimmer et al. |
| 5,274,551 A | 12/1993 | Corby, Jr. | 5,458,718 A | 10/1995 | Venkitachalam |
| 5,279,309 A | 1/1994 | Taylor et al. | 5,464,446 A | 11/1995 | Dreessen et al. |
| 5,285,787 A | 2/1994 | Machida | 5,469,847 A | 11/1995 | Zinreich et al. |
| 5,291,199 A | 3/1994 | Overman et al. | 5,478,341 A | 12/1995 | Cook et al. |
| 5,291,889 A | 3/1994 | Kenet et al. | 5,478,343 A | 12/1995 | Ritter |
| 5,295,483 A | 3/1994 | Nowacki et al. | 5,480,422 A | 1/1996 | Ben-Haim |
| 5,297,549 A | 3/1994 | Beatty et al. | 5,480,439 A | 1/1996 | Bisek et al. |
| 5,299,253 A | 3/1994 | Wessels | 5,483,961 A | 1/1996 | Kelly et al. |
| 5,299,254 A | 3/1994 | Dancer et al. | 5,485,849 A | 1/1996 | Panescu et al. |
| 5,299,288 A | 3/1994 | Glassman et al. | 5,487,391 A | 1/1996 | Panescu |
| 5,300,080 A | 4/1994 | Clayman et al. | 5,487,729 A | 1/1996 | Avellanet et al. |
| 5,305,091 A | 4/1994 | Gelbart et al. | 5,487,757 A | 1/1996 | Truckai et al. |
| 5,305,203 A | 4/1994 | Raab | 5,490,196 A | 2/1996 | Rudich et al. |
| 5,306,271 A | 4/1994 | Zinreich et al. | 5,494,034 A | 2/1996 | Schlondorff et al. |
| 5,307,072 A | 4/1994 | Jones, Jr. | 5,503,416 A | 4/1996 | Aoki et al. |
| 5,309,913 A | 5/1994 | Kormos et al. | 5,513,637 A | 5/1996 | Twiss et al. |
| 5,315,630 A | 5/1994 | Sturm et al. | 5,514,146 A | 5/1996 | Lam et al. |
| 5,316,024 A | 5/1994 | Hirschi et al. | 5,515,160 A | 5/1996 | Schulz et al. |
| 5,318,025 A | 6/1994 | Dumoulin et al. | 5,517,990 A | 5/1996 | Kalfas et al. |
| 5,320,111 A | 6/1994 | Livingston | 5,531,227 A | 7/1996 | Schneider |
| 5,325,728 A | 7/1994 | Zimmerman et al. | 5,531,520 A | 7/1996 | Grimson et al. |
| 5,325,873 A | 7/1994 | Hirschi et al. | 5,542,938 A | 8/1996 | Avellanet et al. |
| 5,329,944 A | 7/1994 | Fabian et al. | 5,543,951 A | 8/1996 | Moehrmann |
| 5,330,485 A | 7/1994 | Clayman et al. | 5,546,940 A | 8/1996 | Panescu et al. |
| 5,333,168 A | 7/1994 | Fernandes et al. | 5,546,949 A | 8/1996 | Frazin et al. |

| | | | | | | |
|---|---|---|---|---|---|---|
| 5,546,951 | A | 8/1996 | Ben-Haim | 5,767,669 | A | 6/1998 | Hansen et al. |
| 5,551,429 | A | 9/1996 | Fitzpatrick et al. | 5,767,960 | A | 6/1998 | Orman |
| 5,558,091 | A | 9/1996 | Acker et al. | 5,769,789 | A | 6/1998 | Wang et al. |
| 5,566,681 | A | 10/1996 | Manwaring et al. | 5,769,843 | A | 6/1998 | Abela et al. |
| 5,568,384 | A | 10/1996 | Robb et al. | 5,769,861 | A | 6/1998 | Vilsmeier |
| 5,568,809 | A | 10/1996 | Ben-haim | 5,772,594 | A | 6/1998 | Barrick |
| 5,572,999 | A | 11/1996 | Funda et al. | 5,775,322 | A | 7/1998 | Silverstein et al. |
| 5,573,533 | A | 11/1996 | Strul | 5,776,064 | A | 7/1998 | Kalfas et al. |
| 5,575,794 | A | 11/1996 | Walus et al. | 5,782,765 | A | 7/1998 | Jonkman |
| 5,575,798 | A | 11/1996 | Koutrouvelis | 5,787,886 | A | 8/1998 | Kelly et al. |
| 5,583,909 | A | 12/1996 | Hanover | 5,792,055 | A | 8/1998 | McKinnon |
| 5,588,430 | A | 12/1996 | Bova et al. | 5,795,294 | A | 8/1998 | Luber et al. |
| 5,590,215 | A | 12/1996 | Allen | 5,797,849 | A | 8/1998 | Vesely et al. |
| 5,592,939 | A | 1/1997 | Martinelli | 5,799,055 | A | 8/1998 | Peshkin et al. |
| 5,595,193 | A | 1/1997 | Walus et al. | 5,799,099 | A | 8/1998 | Wang et al. |
| 5,596,228 | A | 1/1997 | Anderton et al. | 5,800,352 | A | 9/1998 | Ferre et al. |
| 5,600,330 | A | 2/1997 | Blood | 5,800,535 | A | 9/1998 | Howard, III |
| 5,603,318 | A | 2/1997 | Heilbrun et al. | 5,802,719 | A | 9/1998 | O'Farrell, Jr. et al. |
| 5,611,025 | A | 3/1997 | Lorensen et al. | 5,803,089 | A | 9/1998 | Ferre et al. |
| 5,617,462 | A | 4/1997 | Spratt | 5,807,252 | A | 9/1998 | Hassfeld et al. |
| 5,617,857 | A | 4/1997 | Chader et al. | 5,810,008 | A | 9/1998 | Dekel et al. |
| 5,619,261 | A | 4/1997 | Anderton | 5,810,728 | A | 9/1998 | Kuhn |
| 5,622,169 | A | 4/1997 | Golden et al. | 5,810,735 | A | 9/1998 | Halperin et al. |
| 5,622,170 | A | 4/1997 | Schulz | 5,820,553 | A | 10/1998 | Hughes |
| 5,627,873 | A | 5/1997 | Hanover et al. | 5,823,192 | A | 10/1998 | Kalend et al. |
| 5,628,315 | A | 5/1997 | Vilsmeier et al. | 5,823,958 | A | 10/1998 | Truppe |
| 5,630,431 | A | 5/1997 | Taylor | 5,828,725 | A | 10/1998 | Levinson |
| 5,636,644 | A | 6/1997 | Hart et al. | 5,828,770 | A | 10/1998 | Leis et al. |
| 5,638,819 | A | 6/1997 | Manwaring et al. | 5,829,444 | A | 11/1998 | Ferre et al. |
| 5,640,170 | A | 6/1997 | Anderson | 5,831,260 | A | 11/1998 | Hansen |
| 5,642,395 | A | 6/1997 | Anderton et al. | 5,833,608 | A | 11/1998 | Acker |
| 5,643,268 | A | 7/1997 | Vilsmeier et al. | 5,834,759 | A | 11/1998 | Glossop |
| 5,645,065 | A | 7/1997 | Shapiro et al. | 5,836,954 | A | 11/1998 | Heilbrun et al. |
| 5,646,524 | A | 7/1997 | Gilboa | 5,840,024 | A | 11/1998 | Taniguchi et al. |
| 5,647,361 | A | 7/1997 | Damadian | 5,840,025 | A | 11/1998 | Ben-Haim |
| 5,662,111 | A | 9/1997 | Cosman | 5,843,076 | A | 12/1998 | Webster, Jr. et al. |
| 5,664,001 | A | 9/1997 | Tachibana et al. | 5,848,967 | A | 12/1998 | Cosman |
| 5,674,296 | A | 10/1997 | Bryan et al. | 5,851,183 | A | 12/1998 | Bucholz |
| 5,676,673 | A | 10/1997 | Ferre et al. | 5,865,846 | A | 2/1999 | Bryan et al. |
| 5,681,260 | A | 10/1997 | Ueda et al. | 5,868,674 | A | 2/1999 | Glowinski et al. |
| 5,682,886 | A | 11/1997 | Delp et al. | 5,868,675 | A | 2/1999 | Henrion et al. |
| 5,682,890 | A | 11/1997 | Kormos et al. | 5,871,445 | A | 2/1999 | Bucholz |
| 5,690,108 | A | 11/1997 | Chakeres | 5,871,455 | A | 2/1999 | Ueno |
| 5,694,945 | A | 12/1997 | Ben-Haim | 5,871,487 | A | 2/1999 | Warner et al. |
| 5,695,500 | A | 12/1997 | Taylor et al. | 5,873,822 | A | 2/1999 | Ferre et al. |
| 5,695,501 | A | 12/1997 | Carol et al. | 5,880,976 | A | 3/1999 | Digioia, III et al. |
| 5,697,377 | A | 12/1997 | Wittkampf | 5,882,304 | A | 3/1999 | Ehnholm et al. |
| 5,702,406 | A | 12/1997 | Vilsmeier et al. | 5,884,410 | A | 3/1999 | Prinz |
| 5,711,299 | A | 1/1998 | Manwaring et al. | 5,889,834 | A | 3/1999 | Vilsmeier et al. |
| 5,713,946 | A | 2/1998 | Ben-Haim | 5,891,034 | A | 4/1999 | Bucholz |
| 5,715,822 | A | 2/1998 | Watkins | 5,891,157 | A | 4/1999 | Day et al. |
| 5,715,836 | A | 2/1998 | Kliegis et al. | 5,904,691 | A | 5/1999 | Barnett et al. |
| 5,718,241 | A | 2/1998 | Ben-Haim et al. | 5,907,395 | A | 5/1999 | Schultz et al. |
| 5,727,552 | A | 3/1998 | Ryan | 5,913,820 | A | 6/1999 | Bladen et al. |
| 5,727,553 | A | 3/1998 | Saad | 5,920,395 | A | 7/1999 | Schulz |
| 5,729,129 | A | 3/1998 | Acker | 5,921,992 | A | 7/1999 | Costales et al. |
| 5,730,129 | A | 3/1998 | Darrow et al. | 5,923,727 | A | 7/1999 | Navab |
| 5,730,130 | A | 3/1998 | Fitzpatrick et al. | 5,928,248 | A | 7/1999 | Acker |
| 5,732,703 | A | 3/1998 | Kalfas et al. | 5,938,603 | A | 8/1999 | Ponzi |
| 5,735,278 | A | 4/1998 | Hoult et al. | 5,938,694 | A | 8/1999 | Jaraczewski et al. |
| 5,738,096 | A | 4/1998 | Ben-Haim | 5,947,980 | A | 9/1999 | Jensen et al. |
| 5,740,802 | A | 4/1998 | Nafis et al. | 5,947,981 | A | 9/1999 | Cosman |
| 5,741,214 | A | 4/1998 | Ouchi et al. | 5,950,629 | A | 9/1999 | Taylor et al. |
| 5,742,394 | A | 4/1998 | Hansen | 5,951,475 | A | 9/1999 | Gueziec et al. |
| 5,744,953 | A | 4/1998 | Hansen | 5,951,571 | A | 9/1999 | Audette |
| 5,748,767 | A | 5/1998 | Raab | 5,954,647 | A | 9/1999 | Bova et al. |
| 5,749,362 | A | 5/1998 | Funda et al. | 5,954,796 | A | 9/1999 | McCarty et al. |
| 5,749,835 | A | 5/1998 | Glantz | 5,957,844 | A | 9/1999 | Dekel et al. |
| 5,752,513 | A | 5/1998 | Acker et al. | 5,967,980 | A | 10/1999 | Ferre et al. |
| 5,755,725 | A | 5/1998 | Druais | 5,967,982 | A | 10/1999 | Barnett |
| RE35,816 | E | 6/1998 | Schulz | 5,968,047 | A | 10/1999 | Reed |
| 5,758,667 | A | 6/1998 | Slettenmark | 5,971,997 | A | 10/1999 | Guthrie et al. |
| 5,762,064 | A | 6/1998 | Polyani | 5,976,156 | A | 11/1999 | Taylor et al. |

| | | | | | | |
|---|---|---|---|---|---|---|
| 5,980,535 | A | 11/1999 | Barnett et al. | 6,694,162 B2 | 2/2004 | Hartlep |
| 5,983,126 | A | 11/1999 | Wittkampf | 6,701,179 B1 | 3/2004 | Martinelli et al. |
| 5,987,349 | A | 11/1999 | Schulz | 2001/0007918 A1 | 7/2001 | Vilsmeier et al. |
| 5,987,960 | A | 11/1999 | Messner et al. | 2002/0095081 A1 | 7/2002 | Vilsmeier |
| 5,999,837 | A | 12/1999 | Messner et al. | 2004/0024309 A1 | 2/2004 | Ferre et al. |
| 5,999,840 | A | 12/1999 | Grimson et al. | 2004/0097952 A1 | 5/2004 | Kumar et al. |
| 6,001,130 | A | 12/1999 | Bryan et al. | 2004/0171924 A1 * | 9/2004 | Mire et al. .................. 600/407 |
| 6,006,126 | A | 12/1999 | Cosman | | | |
| 6,006,127 | A | 12/1999 | Van Der Brug et al. | | | |

FOREIGN PATENT DOCUMENTS

| | | |
|---|---|---|
| DE | 30 42 343 A1 | 6/1982 |
| DE | 35 08 730 | 3/1985 |
| DE | 37 17 871 | 5/1987 |
| DE | 38 38 011 | 11/1988 |
| DE | 38 31 278 A1 | 3/1989 |
| DE | 42 13 426 | 4/1992 |
| DE | 42 25 112 | 7/1992 |
| DE | 42 33 978 C1 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 10085137 | 11/2002 |
| DE | 10239710 | 3/2004 |
| EP | 0 062 941 | 3/1982 |
| EP | 0 119 660 | 9/1984 |
| EP | 0 155 857 | 1/1985 |
| EP | 0 319 844 A1 | 1/1988 |
| EP | 0 326 768 | 12/1988 |
| EP | 0419729 A1 | 9/1989 |
| EP | 0350996 A1 | 1/1990 |
| EP | 0 651 968 A1 | 8/1990 |
| EP | 0 427 358 | 10/1990 |
| EP | 0 456 103 | 5/1991 |
| EP | 0 581 704 B1 | 7/1993 |
| EP | 0655138 B1 | 8/1993 |
| EP | 0894473 A2 | 1/1995 |
| EP | 0 908 146 | 10/1998 |
| EP | 0 930 046 | 10/1998 |
| EP | 1442729 | 8/2004 |
| EP | 1449485 | 8/2004 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 4/1991 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |

| | | | |
|---|---|---|---|
| 6,013,087 | A | 1/2000 | Adams et al. |
| 6,014,580 | A | 1/2000 | Blume et al. |
| 6,016,439 | A | 1/2000 | Acker |
| 6,019,725 | A | 2/2000 | Vesely et al. |
| 6,024,695 | A | 2/2000 | Taylor et al. |
| 6,050,724 | A | 4/2000 | Schmitz et al. |
| 6,059,718 | A | 5/2000 | Taniguchi et al. |
| 6,063,022 | A | 5/2000 | Ben-Haim |
| 6,071,288 | A | 6/2000 | Carol et al. |
| 6,073,043 | A | 6/2000 | Schneider |
| 6,076,008 | A | 6/2000 | Bucholz |
| 6,096,050 | A | 8/2000 | Audette |
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier |
| 6,233,476 | B1 | 5/2001 | Strommer et al. |
| 6,246,231 | B1 | 6/2001 | Ashe |
| 6,259,942 | B1 | 7/2001 | Westermann et al. |
| 6,273,896 | B1 | 8/2001 | Franck et al. |
| 6,285,902 | B1 | 9/2001 | Kienzle, III et al. |
| 6,298,262 | B1 | 10/2001 | Franck et al. |
| 6,314,310 | B1 | 11/2001 | Ben-Haim et al. |
| 6,332,089 | B1 | 12/2001 | Acker et al. |
| 6,341,231 | B1 | 1/2002 | Ferre et al. |
| 6,351,659 | B1 | 2/2002 | Vilsmeier |
| 6,381,485 | B1 | 4/2002 | Hunter et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,499,488 | B1 | 12/2002 | Hunter et al. |
| 6,516,046 | B1 | 2/2003 | Fröhlich et al. |
| 6,527,443 | B1 | 3/2003 | Vilsmeier et al. |
| 6,551,325 | B2 | 4/2003 | Neubauer et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |

| | | |
|---|---|---|
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO 01/30437 A1 | 5/2001 |
| WO | WO 02062248 | 8/2002 |
| WO | WO 03096870 | 11/2003 |
| WO | WO 2004/030555 | 4/2004 |

OTHER PUBLICATIONS

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hatch, "Reference-Display System for the Integration of CT Scanning and the Operating Microscope," Thesis, Thayer School of Engineering, Oct. 1984, pp. 1-189.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Computer-assisted stereotaxic laser resection of intraaxial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128.

Germano, "Instrumentation, Technique and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

International Search report for PCT/US2005/039928.

Adams et al., Computer-Assisted Surgery, IEEE Computer Graphics & Applications, pp. 43-51, (May 1990).

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., Jr. et al, Optical localization for interactive, image-guided neurosurgery, SPIE, vol. 2164, pp. 137-145 (undated.

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Guthrie, B.L., Graphic-Interactive Cranial Surgery: The Operating Arm System, Handbook of Stereotaxy Using the CRW Apparatus, Chapter 13, pp. 193-211 (undated.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Computer-Directed Stereotactic Resection of Brain Tumors, Neurologica Operative Atlas, vol. 1, No. 4, pp. 299-313 (1991).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed. Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobaugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

* cited by examiner

METHOD AND APPARATUS FOR CALIBRATING NON-LINEAR INSTRUMENTS

FIELD

The present invention relates generally to navigated surgery, and more specifically, to a method and apparatus for calibrating attachments for non-linear instruments to a tracking sensor on the instrument and navigating the attachment during a procedure.

BACKGROUND

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require a dynamic reference frame to track the position of the patient should patient movement occur during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure.

Various instruments may be used during an operative procedure that are desired to be tracked. Image data is generally acquired, either intra-operatively or pre-operatively, and the instrument is generally illustrated, and superimposed on the captured image data to identify the position of the instrument relative to the patient space. Therefore, the instrument may include tracking sensors, such as electromagnetic coils or optical detection points, such as LEDs or reflectors, that may be detected by a suitable tracking system.

Other types of navigation systems operate as an image-less system, where an image of the body is not captured by an imaging device prior to the medical procedure, such as the device disclosed in U.S. patent application Ser. No. 10/687, 539, entitled Method And Apparatus For Surgical Navigation Of A Multiple Piece Construct For Implantation, filed Oct. 16, 2003, incorporated herein by reference. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model.

Most types of orthopedic medical procedures are performed using conventional surgical techniques, such as spine, hip, knee, shoulder, a synovial joint, and a facet joint. These techniques generally involve opening the patient in a manner to provide adequate viewing by the surgeon during the medical procedure. Use of the navigated procedure may enable more precise and accurate placement of an implant within the patient and may also enable surgery with diminished visualization.

Image guided procedures generally require the use of instruments and other portions that are tracked with the aid of tracking sensors. The tracking sensors, however, are generally affixed to the instrument. Thus the position of an attachment to the instrument, such as an implant or reamer, is known only through knowing the position of the instrument. Thus the tracking system must be calibrated for each of the attachments. If the instrument is straight, cylindrical, and the attachment is concentric, this can be done by touching the end point on the attachment with a tracked probe and then rotating the instrument about its axis in a tracked calibration block to determine the axis of the cylindrical shaft. Often, however, the instruments are not straight and it is desirable to still calibrate the attachment in the tracking system.

SUMMARY

A method and apparatus for performing a calibration and navigation of a member. The member may be calibrated relative to a selected portion, such as a sensor on an instrument. The calibrated member may then be navigated with a selected system. The calibration technique can be infinitely flexible and not rigid or designed for specific components.

In particular an attachment may be calibrated to an instrument when the instrument is not linear. The attachment may be touched in several points with a tracked probe and the tracking system may determine the position of the touched points relative to a tracking sensor affixed to the instrument. Various techniques may be used to calibrate the attachment. The calibration allows for navigating the attachment in patient space with a tracking system.

According to various embodiments a system to navigate an instrument relative to a portion of a patient's anatomy is taught. The system may include an instrument including an engaging end, a working end, and a shaft extending between the engaging end and the working end. A member may be provided to selectively engage the engaging end such that the member is operable to be engaged and disengaged from the engaging end. A first sensor may be interconnected with the instrument. Also, a tracking system may track the first sensor and the second sensor. The tracking system is operable to determine an orientation relative to the first sensor when the member is engaged to the engaging end.

According to various embodiments a method of determining a position of a member relative to an instrument is taught. The method includes interconnecting a first tracking sensor and the instrument and also interconnecting the member and the instrument. A plane of the member may be determined. Also, a vector of the member may be determined.

According to various embodiments a method of navigating a procedure relative to an anatomy of a patient is disclosed. The method may include interconnecting a first tracking sensor and the instrument and interconnecting the member and the instrument. At least three points are defined by the member that define a plane that may be determined. Also a fourth point to define a depth and start point for a vector normal to the plane relative to the member may be determined. The member may be navigated relative to the anatomy based at least in part on the plane and the vector.

Further areas of applicability will become apparent from the description provided hereinafter. It should be understood that the description and various examples, while indicating various embodiments, are intended for purposes of illustration only and are not intended to limit the scope of the description or the present teachings.

BRIEF DESCRIPTION OF THE DRAWINGS

The present teachings will become more fully understood from the detailed description and the accompanying drawings, wherein.

DETAILED DESCRIPTION OF VARIOUS EMBODIMENTS

The following description of various embodiments is merely exemplary in nature and is in no way intended to limit the teachings, its application, or uses. As indicated above, the present invention is directed at providing improved, calibration for non-linear instruments when attachment members are connected thereto. Although the following discussion relates to an acetabular reamer and/or an acetabular implant it will be understood that any appropriate attachment, instrument or surgical procedure may be used.

Figure 1:
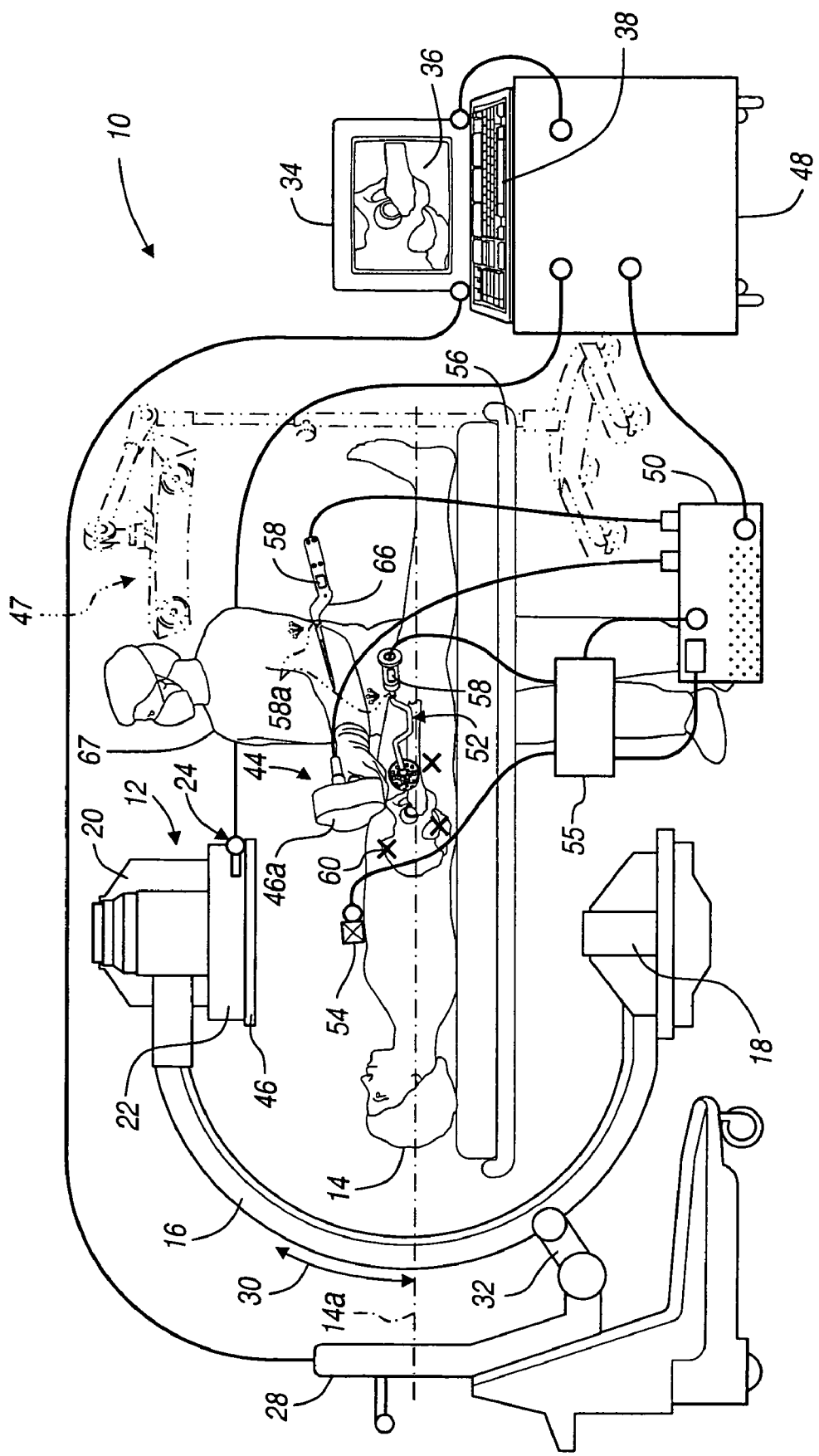
FIG. 1 is a diagram of a navigation system according to various teachings of the present invention.

FIG. 1 is a diagram illustrating an overview of an image-guided navigation system 10 for use in positioning an attachment, such as a reamer head, a prosthesis, or other portion. It should further be noted that the navigation system 10 may be used to navigate any type of instrument, implant, or delivery system, including: guide wires, arthroscopic systems, orthopedic implants, etc. Moreover, these instruments may be used to navigate or map any region of the body. The navigation system 10 and the various instruments may be used in any appropriate procedure, such as one that is generally minimally invasive or an open procedure.

The navigation system 10 may include an optional imaging device 12 that is used to acquire pre-, intra-, or post-operative or real-time image data of a patient 14. Alternatively various imageless systems may be used or images using atlas models for producing patient images, such as those disclosed in U.S. patent application Ser. No. 10/687,539, filed 10/16/2003, entitled "METHOD AND APPARATUS FOR SURGICAL NAVIGATION OF A MULTIPLE PIECE CONSTRUCT FOR IMPLANTATION", herein incorporated by reference. The optional imaging device 12 is, for example, a fluoroscopic x-ray imaging device that may be configured as a C-arm 16 having an x-ray source 18, an x-ray receiving section 20, an optional calibration and tracking target 22 and optional radiation sensors 24.

Image data may also be acquired using other imaging devices, such as those discussed above and herein. The calibration and tracking target 22 includes calibration markers 26 (see FIGS. 2A-2B), further discussed herein. An optional imaging device controller 28, that may control the C-arm 16, can capture the x-ray images received at the receiving section 20 and store the images for later use. The controller 28 may also be separate from the C-arm 16 and/or control the rotation of the C-arm 16. For example, the C-arm 16 may move in the direction of arrow 30 or rotate about a longitudinal axis 14a of the patient 14, allowing anterior or lateral views of the patient 14 to be imaged. Each of these movements involves rotation about a mechanical axis 32 of the C-arm 16.

In the example of FIG. 1, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the optional imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. It will be understood that the tracking target need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data. Receiving section 20 may also be a digital device that converts x-rays directly to digital image data for forming images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for various procedures. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking.

The image data is then forwarded from the C-arm controller 28 to a navigation computer controller or work station 34 having a display 36 and a user interface 38. It will also be understood that the image data is not necessarily first retained in the controller 28, but may also be directly transmitted to the navigation computer 34. The work station 34 provides facilities for displaying the image data as an image on the display 36, saving, digitally manipulating, or printing a hard copy image of the of the received image data. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2B:
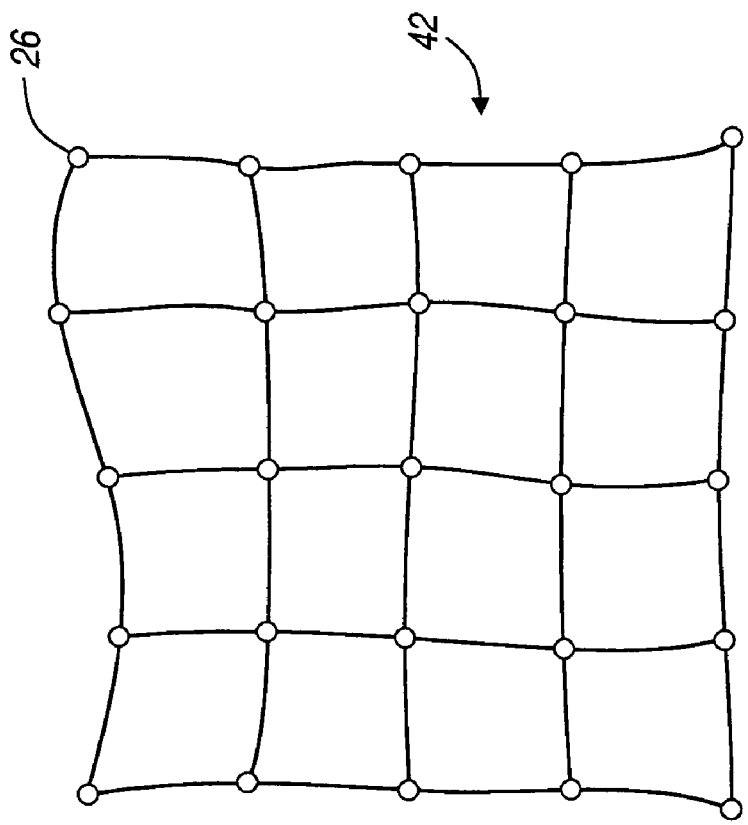
FIGS. 2A and 2B are diagrams representing undistorted and distorted views from a fluoroscopic imaging device.
Figure 2A:
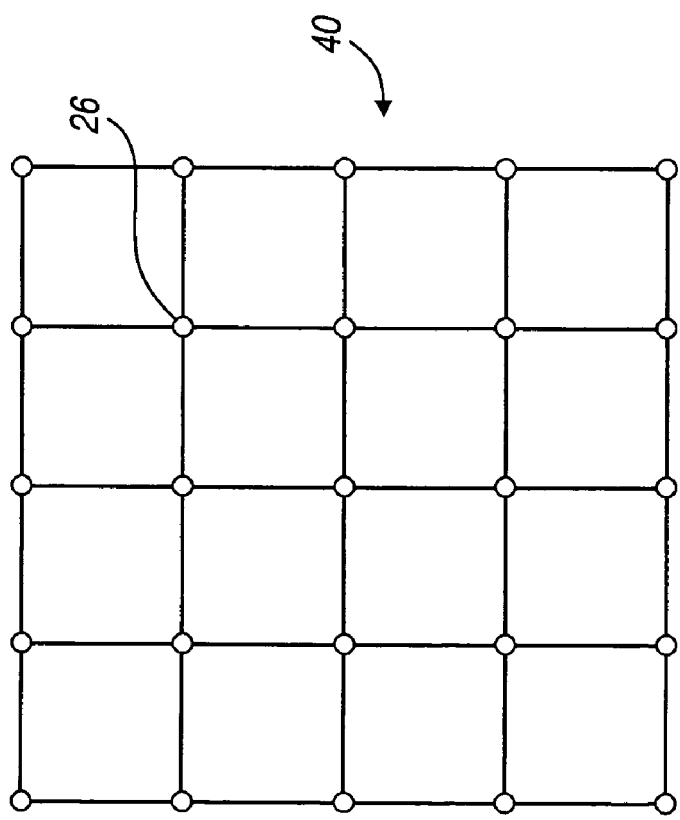

The optional imaging device 12, such as the fluoroscopic C-arm 16, that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 40 of the checkerboard arranged calibration markers 26. The image taken by the receiving section 20, however, can suffer from distortion, as illustrated by the distorted calibration marker image 42, shown in FIG. 2B.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 2A). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intravascular ultrasound (IVUS), ultrasound, intra-operative CT or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 1, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, or other instrument, introduced and advanced in the patient 14, may be superimposed in more than one view on display 36 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction using dynamic reference frames.

Ultrasound imaging is also generally intra-operative procedure using a non-ionizing field to provide either 2D, 3D, or 4D imaging, including anatomy and blood flow information. Ultrasound imaging provides automatic registration and does not need to account for any motion correction.

With continuing reference to FIG. 1, the navigation system 10 further includes an electromagnetic navigation or tracking system 44 that includes a localizer, such as a transmitter coil array 46, the coil array controller 48, a navigation probe interface 50, an instrument 52 and a dynamic reference frame 54. The instrument 52 may be an any appropriate instrument, such as an instrument for preparing a portion of the patient or positioning an implant. The transmitter coil array 46 may also be supplemented or replaced with a mobile localizer 46a. The mobile localizer 46a may be one such as that described in Unofficial U.S. patent application Ser. No. 10/941,782, filed Sep. 15, 2004, and entitled "METHOD AND APPARATUS FOR SURGICAL NAVIGATION", herein incorporated by reference. It will be understood that the tracking system may be any appropriate tracking system, such as an optical localizer illustrated in phantom at 47 such as the StealthStation® TRIA™ sold by Medtronic Surgical Navigation Technology of Louisville, Colo. Other localization systems include, an acoustic, radiation etc.

Further included in the navigation system 10 may be an isolator circuit or box 55. The isolator circuit or box 55 may be included in a transmission line to interrupt a line carrying a signal or a voltage to the navigation probe interface 50. Alternatively, the isolator circuit included in the isolator box 55 may be included in the navigation probe interface 50, the instrument 52, the dynamic reference frame 54, the transmission lines coupling the devices, or any other appropriate location. The isolator box 55 is operable to isolate any of the instruments or patient coincidence instruments or portions that are in contact with the patient should an undesirable electrical surge or voltage take place.

It should further be noted that the entire tracking system 44 or parts of the tracking system 44 may be incorporated into the imaging device 12, including the work station 34 and radiation sensors 24. Incorporating the tracking system 44 may provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 may also be positioned in the items being navigated, further discussed herein. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in a sensor 58 positioned on or in the instrument 52. These induced signals from the instrument 52 are delivered to the navigation probe interface 50 through the isolation circuit 55 and subsequently forwarded to the coil array controller 48. The navigation probe interface 50 may provide all the necessary electrical isolation for the navigation system 10. Alternatively, the electrical isolation may also be provided in the isolator box 55. Nevertheless, the isolator assembly 55 may be included in the navigation probe interface 50 or may be integrated into the instrument 52, and any other appropriate location. The navigation probe interface 50 also includes amplifiers, filters and buffers required to directly interface with the sensors 58 in the instrument 52. Alternatively, the instrument 52 may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

The instrument 52, as will be described in detail below, is equipped with at least one, and generally multiple, tracking sensors 58, that may also be referred to as localization sensors. The instrument 52 can be a handle or inserter that interconnects with an attachment and may assist in placing an implant or in driving a portion. The instrument 52 can include a graspable or manipulable portion at a proximal end and the tracking sensor 58 may be fixed near the manipulable portion of the instrument 52. The tracking sensor 58 may be any appropriate tracking sensor 58 such as an optical sensor, acoustic sensor, or an electromagnetic sensor. If the sensor 58 includes an electromagnetic sensor the electromagnetic field generated by the transmitter coil array 46 may induce a current in the electromagnetic sensor 58. An alternative sensor may include an optical sensor, such as the optical sensor 58a, and may be used in addition to or in place of the electromagnetic sensor 58. The optical sensor may work with the optional optical array 47.

In an alternate embodiment, the electromagnetic sources or generators may be located within the instrument 52 and one or more receiver coils may be provided externally to the patient 14 forming a receiver coil array similar to the transmitter coil array 46. In this regard, the tracking sensors 58 could generate electromagnetic fields that would be received by the receiving coils in the receiving coil array similar to the transmitter coil array 46. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the tracking system 44 is also coupled to the navigation probe interface 50 to forward the information to the coil array controller 48. The dynamic reference frame 54, according to various embodiments, is a small magnetic field detector. The dynamic reference frame 54 may be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 may be any appropriate tracking sensor used as the dynamic reference frame 54 in the navigation system 10. Therefore the dynamic reference frame 54 may also be optical, acoustic, etc. If the dynamic reference frame 54 is electromagnetic it can be configured as a pair of orthogonally oriented coils, each having the same center or may be configured in any other non-coaxial or co-axial coil configurations.

The dynamic reference frame 54 may be affixed externally to the patient 14, adjacent to the region of navigation, such as on the patient's chest, as shown in FIG. 1. The dynamic reference frame 54 can be affixed to the patient's skin, by way of a selected adhesive patch and/or a tensioning system. The dynamic reference frame 54 may also be removably attachable to fiducial markers 60 also positioned on the patient's body and further discussed herein.

The dynamic reference frame 54 may also be attached to various boney portions such as a femur, pelvis, cranium, or other boney portions. The movement of various portions, such as the instrument 52, relative to these boney portions can then be determined, even if the boney portion is also moved. This may assist in positioning an implant or in performing a planned procedure.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the instrument 52 or a pointing device or probe 66 is used, the work station 34 in combination with the coil array controller 48 and the C-arm controller 28 uses the translation map to identify the corresponding point on the pre-acquired image or atlas model, which is displayed on display 36. This identification is known as navigation or localization. An icon representing the localized point or instruments are shown on the display 36 within several two-dimensional image planes, as well as on three and four dimensional images and models.

To enable navigation, the navigation system 10 must be able to detect both the position of the patient's anatomy and the position of the instrument 52 or attachment member attached to the instrument 52. Knowing the location of these two items allows the navigation system 10 to compute and display the position of the instrument 52 in relation to the patient 14. The tracking system 44 is employed to track the instrument 52 and the anatomy simultaneously.

The tracking system 44, if it is using an electromagnetic tracking assembly, essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the tracking sensor 58 location. The dynamic reference frame 54 is fixed to the patient 14 to identify the location of the patient in the navigation field. The electromagnetic tracking system 44 continuously recomputes the relative position of the dynamic reference frame 54 and the instrument 52 during localization and relates this spatial information to patient registration data to enable image guidance of the instrument 52 within and/or relative to the patient 14.

Patient registration is the process of determining how to correlate the position of the instrument 52 relative to the patient 14 to the position on the diagnostic or pre-acquired images. To register the patient 14, a physician or user 67 may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54, such as those disclosed in U.S. Pat. No. 6,381,485, entitled "Registration of Human Anatomy Integrated for Electromagnetic Localization," issued Apr. 30, 2002, herein incorporated by reference.

The system 10 may also perform registration using anatomic surface information or path information as is known in the art. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient and patient space. Generally, the navigation system allows the images on the display 36 to be registered and accurately display the real time location of the various instruments, such as the instrument 52, and other appropriate items, such as the pointer 66. In addition, the pointer 66 may be used to register the patient space to the pre-acquired images or the atlas or 3D models. In addition, the dynamic reference frame 54 may be used to ensure that any planned or unplanned movement of the patient or the transmitter coil array 46 is determined and used to correct the image on the display 36.

Figure 3:
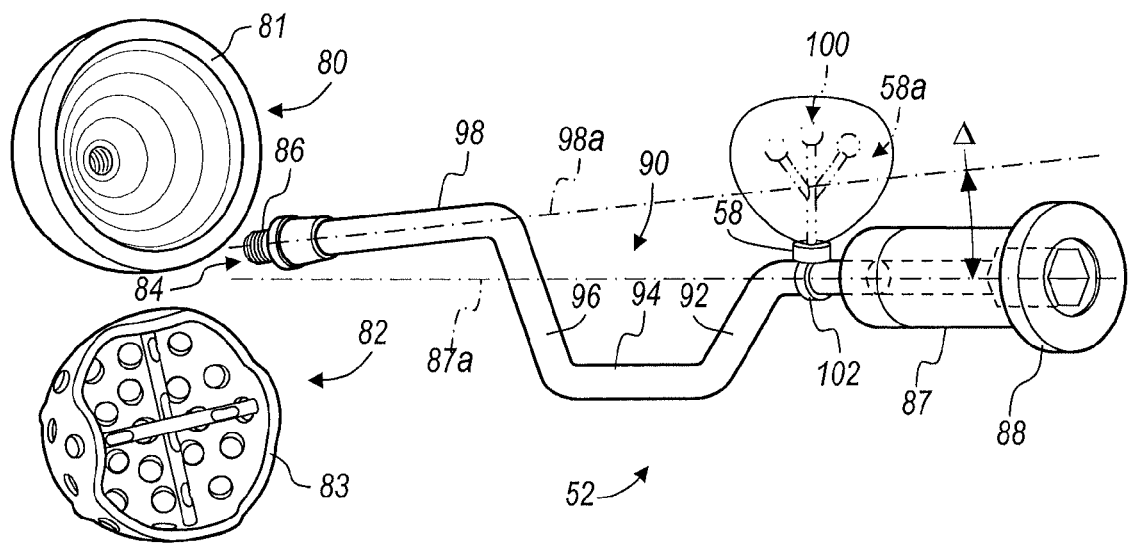
FIG. 3 is a perspective view of an instrument and various attachment members according to various embodiments.

With reference to FIG. 3, the instrument 52 may be any appropriate instrument such as an inserter, an impactor, a driver, or combinations thereof. An attachment member may be attached to the instrument 52 for various purposes. An inserter may be used to insert an attachment such as an implant including an acetabular implant or cup 80 that includes a rim 81. The instrument 52 may also be a driver for driving an attachment such as an acetabular reamer 82 that includes a rim or edge 83.

The instrument 52 generally includes an engagement end 84 that is operable to engage the attachment member, such as the implant 80 or the reamer 82. The engagement end 84 may be any appropriate engagement such as an externally threaded portion 86. The engagement end 84 generally extends from a manipulable or graspable portion 87. The graspable portion 87 may also include an impaction area 88 that may be used to impact the implant 80. Alternatively, the graspable portion 87 may be coupled to a selected drive instrument to drive the attachment member, such as the reamer 82. Various mechanisms may be used to transfer the driving force from the graspable region 87 to the engagement end 84 such as with linkages, flexible drive shafts, and the like. Regardless, the engagement end 84 may be driven in a selected manner to operate the reamer 82 for selected purposes, such as those described herein.

A shaft 90 may extend between the graspable portion 87 and the engagement portion 84. The shaft 90 may include various segments such as a first angle segment 92, an offset segment 94 and a second angle segment 96 and a final segment 98. The final segment 98 may be substantially aligned with the handle portion 86 or may be offset therefrom. For example, the graspable portion 87 may define an axis 87$a$ and the final segment 98 an axis 98$a$. A distance $\Delta$ may be a distance between the two axes 87$a$ and 98$a$. Also, the axis 98$a$ of the final segment 98 may be angled relative to the axis 87$a$ of the graspable portion 87. Further, the offset section 94 may be substantially offset, by either an amount equal to, less than or greater than the final segment 98 relative to the graspable portion 87. Regardless, the shaft 90 may be linear or non-linear and/or substantially offset for various purposes.

The angle sections 92, 96 are provided to position the offset section 94 and the final segments 98 in an appropriate orientation relative to the graspable portion 87. The shape of the shaft 90 may be any appropriate shape, size, dimension or the like for various purposes. For example, the shaft 90 may be formed in an appropriate orientation to assist in providing a optimal viewing of a surgical area, positioning relative to soft tissue, or the like of the instrument 52. For example, when positioning the implant 80 relative to an acetabulum it may be desirable to provide clearance around various soft tissues and bony structures to reduce an invasiveness of a procedure for positioning the implant 80. It will be understood that various other purposes may be provided for including the shaft 90 in a selected orientation.

The instrument of 52 may include the electromagnetic tracking sensor 58. It will be understood that although the following discussion is related generally to an electromagnetic tracking sensor 58, other tracking sensors, such as the optical tracking sensor 58$a$, having multiple optical tracking devices 100, may also be used in addition or alternatively to the tracking sensor 58. As mentioned above the tracking sensor 58 may transmit its position in patient space.

The tracking sensor 58 may be affixed to the instrument 52 in any appropriate manner. The tracking sensor 58 may include a amp 102 to amp the tracking sensor 58 to the instrument. The tracking sensor 58 may be affixed to the instrument 52 in any appropriate orientation that may either be keyed or specific or substantially random and may be registered or calibrated after being attached to the instrument 52. Therefore, the tracking sensor 58 may also fit into a threaded portion, keyed portion, or the like on the instrument 52 to hold the tracking sensor 58 in a selected position. Also, the tracking sensor 58 may be provided integrally formed with the instrument 52 or may be affixed to the instrument 52 during an operative procedure.

The tracking sensor 58, however, may be interconnected with any appropriate instrument. It will be understood that the tracking sensor 58 may be affixed to any instrument in any appropriate manner, such as with the amp 102 or other appropriate mechanism. Thus the tracking sensor 58, and the method described herein, may be used with any appropriate instrument. This allows the system to be very flexible and interchangeable for use by a plurality of users and preferences.

The tracking sensor 58 positioned on the instrument 52 is generally held at a fixed position relative to the engagement portion 86 of the instrument 52. Therefore, the navigation system 10 may be used to determine a position of the engagement end 86 or attachment member to the engagement end 86 by reference to the tracking sensor 58. Tracking the instrument 52 may be performed according to any appropriate apparatus or method, such as those described above.

Figure 4:
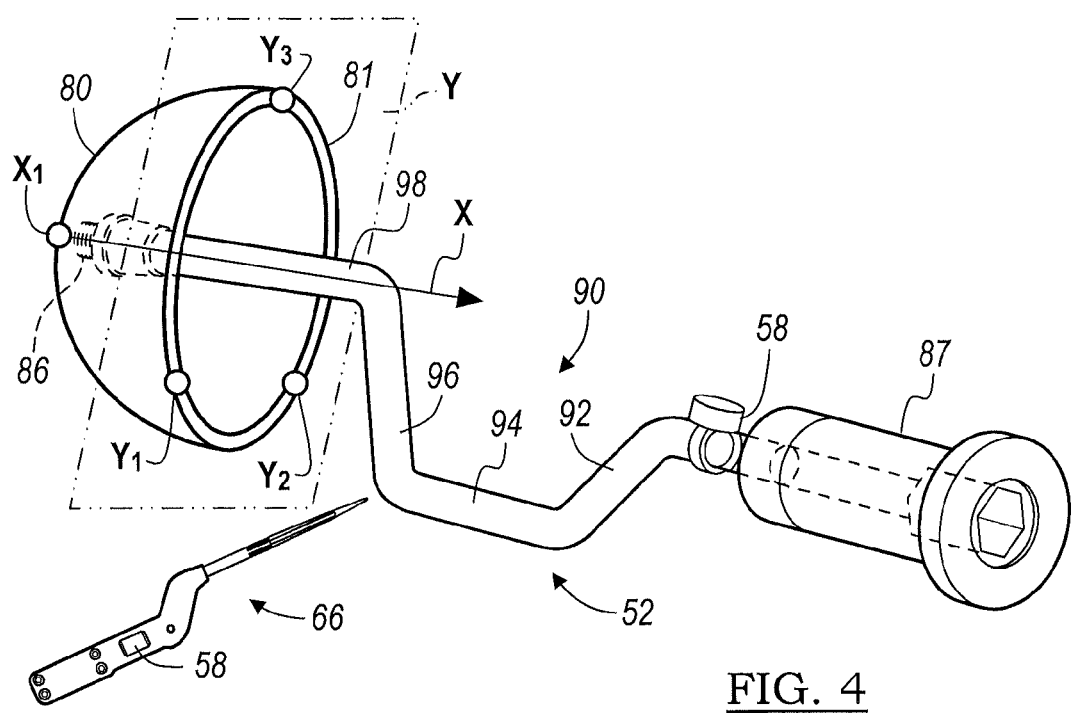
FIG. 4 is a perspective view of the instrument connected to an attachment member according to various embodiment.

With reference to FIG. 4, the probe 66 is illustrated relative to the instrument 52 once the cup 80 is affixed thereto. As described herein the cup 80 may be affixed to the engagement end 86 of the instrument. The probe 66 may then be used to define various portions on the cup 80. The probe 66 may be any appropriate probe and may also include a tracking sensor 58. Further, it will be understood that the probe 66 may be any appropriate probe that may include the optical sensor 58A, an acoustic sensor or the like. The probe 66 may include any appropriate sensor that is operable to work with the tracking system 44 to determine a position of the probe 66 or a portion of the probe 66.

Figure 5:
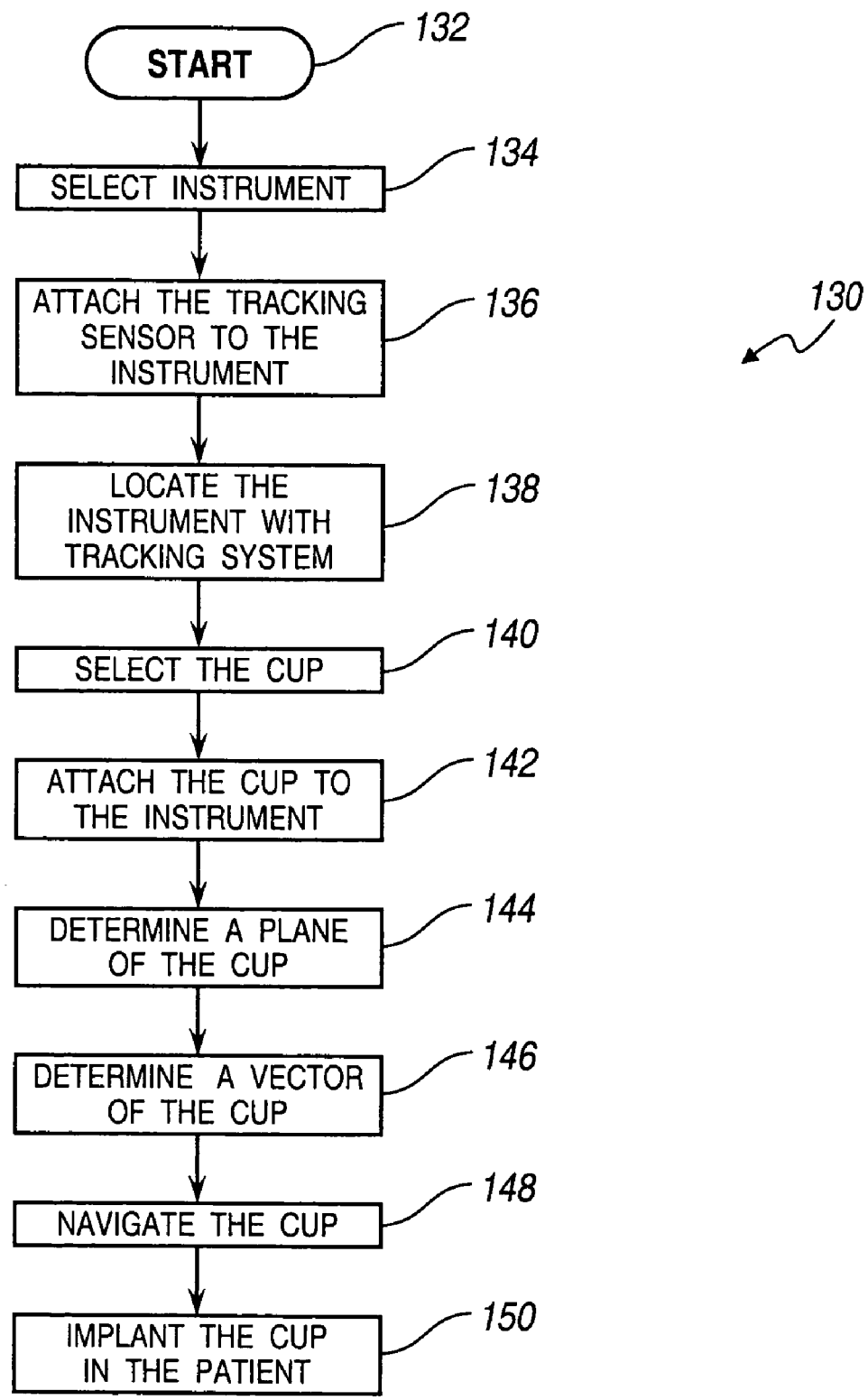
FIG. 5 is a flow chart of calibrating a member in a navigation system according to various embodiments.

With reference to FIGS. 4 and 5, a method of calibrating the selected attachment member, such as the cup 80, relative to the instrument 52 will be described. It will be understood that any appropriate attachment member, such as the reamer 82, or any other member may be registered relative to the instrument 52 may be provided. The instrument 52 may also be any appropriate instrument and may be provided for interconnecting with any selected portion such as any appropriate implant, including orthopedic implants such as hip implants, shoulder implants, spinal implants, knee implants, or the like. Therefore, the description of the method relative to the cup 80 is merely exemplary and not intended to limit the teachings herein.

Once the cup 80 has been attached to the instrument 52 in any appropriate manner, such as interconnecting the cup 80 with the attachment section 86 using threads, the cup 80 may be calibrated and/or registered relative to the tracking sensor 58 attached to the instrument 52. The probe 66 may be used to interact with the cup 80 and the tracking sensor 58 with the tracking system 44 to determine a plane Y of the cup 80. The plane Y may be determined according to any appropriate method, such as those described herein. Regardless, the tracking system 44 is operable to determine a position of the plane Y relative to the cup 80 for assisting in tracking the cup 80 when moved with the instrument 52. Further, a vector or line X may be determined by various methods in addition to determining the plane Y of the cup 80. The tracking system 44 alone, a user alone, or both together may be used to calculate the plane Y and the vector X.

The plane Y, generally defined by a rim or portion of the cup 80 can be defined by three points $Y_1$, $Y_2$, $Y_3$. The upper portion of the cup 80 generally defines the plane Y. In this way the plane Y can be used to determine a position of the cup 80 relative to the instrument 52 for tracking in patient space. For example the navigation system 10 can use the plane Y to determine a depth of the cup 80 during an implantation procedure. The vector X can be used to determine an orientation or position of the cup 80, also in patient space. The vector X can be any appropriate vector and the relative movement of the vector X to the patient 14 can be determined. The point $X_1$ may be any point on the cup 80 and may be an apex such that a depth of the cup 80 may also be determined. The vector X is generally defined normal to the plane Y through the point $X_1$.

With reference to FIG. 5, a general calibration method 130 is illustrated. The method 130 may be used to determine a plane of the cup 80. Generally, the method 130 starts at block 132. The instrument is selected in block 134 that may include the impaction handle as the instrument 52. It will be understood that any appropriate instrument may be selected such as a driver for driving the reamer 82 or driving any appropriate portion, such as rasp or for impaction of any appropriate implant. Further, the instrument selected in block 134 may include a generally non-linear configuration. Also, a size of an attachment member may be a part of the selection process. For, example, a plurality of the cups 80 may be provided, each of differing sizes. Regardless, the instrument is selected for performing a selected procedure.

A sensor, optionally, may be attached to the instrument. For example, the tracking sensor 58 may be attached to the instrument 52. It will be understood, however, that the instrument 52, such as discussed above, may include an integral sensor and not need a sensor attached thereto. Regardless, a sensor may be attached to the instrument 52 if necessary.

After the tracking sensor 58 is attached to the instrument 52 in block 136, the instrument 52 may be sensed or located with the tracking system 44 in block 138. It will be understood that the instrument 52 need not be located at this time and may be done later, but it may be helpful to locate the instrument 52 after attaching the sensor in block 136. Next, the cup is selected in block 140. As discussed above, the cup may be any appropriate attachment member, such as a reamer or an appropriate implant, including the acetabular cup 80. The acetabular cup 80 is merely exemplary and not intended to limit the teachings herein.

Further, the cup 80 may be any appropriate cup, such as a large, small, or any appropriate size cup. Further, the cup may include a plurality of cups each having distinct sizes. For example, a tray or plurality of cups may include various diameters that range from about 20 mm to about 70 mm. Further, the cups may include depths that range in any appropriate depth. Therefore, the cup selected in block 140 may be any appropriate cup, such as one selected for a specific procedure or a specific patient. Also the cup selected may be a planned cup for selection or one selected after a trialing procedure. Regardless, the cup may be any appropriate cup that is selected for use in a procedure.

The cup 80 may then be attached to the instrument 52 in block 142. The cup 80 may be attached to the instrument 52 in any appropriate manner, such as a thread, locking ring, press fit or the like. It will be understood that the cup 80 may be attached to the instrument 52, or any appropriate cup and instrument combination, in an appropriate manner. Generally, the cup 80 is attached to the instrument 52 to allow for implantation of the cup 80 and subsequent removal of the instrument 52 after implanting the cup 80.

Once the cup 80 is attached to the instrument 52 in block 142, the plane of the cup Y may be determined in block 144, according to any appropriate method, such as those discussed herein. The plane of the cup Y may be determined in any appropriate manner, such as those discussed herein, for use in navigating the cup 80 relative to the patient 14. The plane of the cup Y may generally be a plane defined by the upper rim 81 of the cup 80 and generally defines a proximal edge of the cup. The rim 81 also generally defines an opening or entrance into the cup 80 and defines an edge that may interact with an edge or surface of a boney portion, such as a prepared acetabulum of the pelvis. The plane Y may assist in navigating the cup 80, such as assisting the navigation system 10 in determining a position of the cup 80 relative to the patient 14 during a navigated procedure.

Once the plane Y is determined in block 144, a vector or line X emanating from the cup in block 146 may be determined, according to any appropriate method such as those discussed herein. The vector X may be any appropriate vector defined through the plane Y and generally is substantially normal to the plane Y. Although the vector X may be normal to the plane Y, the vector X may be any appropriate vector for use in the navigation system 10. The vector X merely provides a reference vector relative to the instrument 52 and/or patient 14 for movement of the instrument 52 and the cup 80. Therefore the vector X may any appropriate vector and is used merely for reference in determining a relative position of the cup 80 relative to the patient 14 and the tracking sensor 58 for navigating the cup 80.

Once the plane of the cup Y is determined block 144 and the vector X is determined in block 146, the cup 80 may be navigated in block 148. The navigation of the cup 80 in block 148 may be for any appropriate purpose such as implanting the cup in block 150. The implantation of the cup 80 into the patient 14 in block 150 may be any appropriate implantation. The cup 80 may be implanted into a prepared acetabulum that may be prepared with a reamer, such as the reamer 82. It will be understood that the reamer 82 may be registered relative to the instrument 52 in a manner similar to the registration of the cup 80. The reamer may be attached to the instrument 52 or any appropriate instruments, such as the driver, and registered relative to the tracking sensor 58 affixed to the driver. Therefore, it will be understood that a discussion of the registration of the cup 80 is merely exemplary and not intended to limit the teachings herein.

Figure 6:
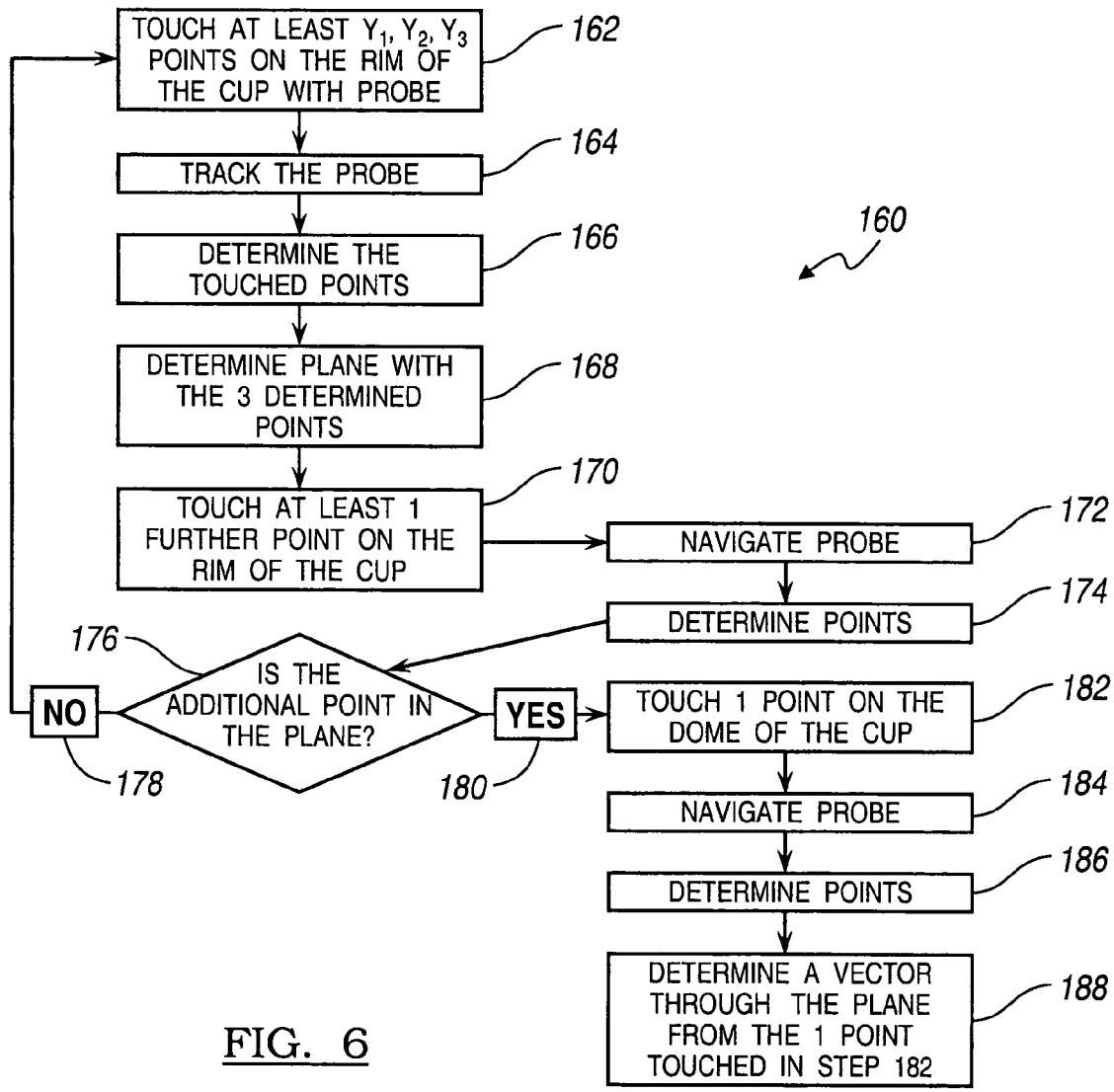
FIG. 6 is a flow chart of determining a plane and a vector calibrating a member in a navigation system according to various embodiments.

With reference to FIG. 6 and additional reference to FIGS. 4 and 5, a method of determining the plane of the cup Y and determining the vector of the cup X will be further described. It will be understood that the method 160 illustrated in FIG. 6 is merely exemplary and not intended to limit the teachings herein.

Once the cup 80 and the tracking sensor 58 have been attached to the instrument, such as in blocks 136 and 142, the plane of the cup Y may be determined in block 144, such as the plane Y, and a vector determined in block 146, such as the vector X, according to the method 130. Initially, touching at least the three points $Y_1$, $Y_2$, and $Y_3$ on the rim of the cup 80 with the probe 66 is performed in block 162. As the user is touching the probe 66 to various points on the rim 81 of the cup 80, the probe 66 can be tracked with the tracking system in block 164. The points touched on the rim 81 may be any appropriate points on the rim 81, such as $Y_1$, $Y_2$, and $Y_3$, of the cup 80. The points may, however, be spread substantially equally around the rim of the cup 81 for calculation efficiencies and accuracy.

The probe is touched to idicia on the member, by the user, and in touching the probe 66 to the plane defining points $Y_1$, $Y_2$, and $Y_3$ on the cup allows the tracking system 44 to determine points on the cup 80. The points $Y_1$, $Y_2$, and $Y_3$, on the rim of the cup may be determined in block 166. The points on the rim of the cup 81 may be any appropriate points and the points may be determined in block 166 by the navigation system 10 including the workstation 34 or any appropriate system. As discussed above because the probe 66 is tracked by the tracking system 44 with the tracking sensor 58 points touched by the probe are known or can be determined by the tracking system 44. Alternatively, the points may be determined by a user, such as touching points on the display 36 or any appropriate method including those described herein.

After the points have been determined in block 166, a plane defined by the points may be determined in block 168. The plane determined in block 168 may be a plane that defines the rim 81 of the cup 80. That is, the plane Y determined by the points $Y_1$, $Y_2$, and $Y_3$, generally defines a flat plane or surface upon which the rim 81 may rest. It will be understood that generally the rim 81 is substantially defined in a single plane.

Nevertheless, it will be understood that the rim 81 may include a raised or non-planar rim and the configuration of the non-planar rim may also be determined by use of the method 130. Rather than determining the single plane Y, a plurality of points may be touched on the rim 81 to substantially map the entire surface of the rim 81. For example, the probe 66 may be drawn along the entire length or circumference of the rim 81 such that a mapping of the rim 81 may be performed. Regardless, if the rim 81 lies substantially in a single plane touching at least three points allows for a determination of the plane Y defined by the three points and, therefore, a plane defined by the rim 81 in block 168.

Once the plane Y has been determined in block 168, either by the user or by the tracking system 44, at least one additional or confirmation point may be touched on the rim 81 in block 170 with the probe 66. The probe may tracked in block 172 as the user touches the confirmation point on the rim 81. The tracking system may then determine the confirmation point touched on block 174. The confirmation point touched on block 170 and determined in block 174 should generally lie on the plane Y determined in block 168. Therefore, touching the additional points in block 170 acts as a check or a confirmation on the plane determined in block 168. Therefore, a determination block 176 includes determining whether the confirmation point in block 174 lies on the plane determined in block 168. If the determination is No in block 178, then additional points are touched in block 162 and the process is repeated until the Yes determination in block 180 is reached. Therefore, the plane Y determined in block 168 can include a confirmation step to ensure that the plane is proper and actually defines the plane of the rim 81.

Once the plane determined in block 168 is confirmed in block 180, an additional or vector point $X_1$ may be touched on the dome of the cup 80 in block 182. The vector point $X_1$ may be touched on the dome of the cup 80 with the probe 66 and the probe may be navigated in block 184. The navigation system 10 may determine the point touched in block 186 so that an additional point on the dome of the cup may be determined relative to the plane Y defining the rim of the cup 81. The vector point $X_1$ determined in block 186 may be used to determine a vector X through the plane Y in block 188. The point $X_1$ may be used to define an origin of the vector X that is normal to the plane Y. The vector X may be determined by a processor, such as one in the workstation, or by the user.

The vector X extending from the vector point $X_1$ touched on the dome of the cup through the plane Y may be any appropriate vector. For example, the additional point touched in block 182 may be a point substantially defining an apex or top of the cup 80 such that the vector X is substantially through a center of the cup 80. In this situation the vector point $X_1$ may also be used to determine a depth of the cup 80 as well. That is the point $X_1$ may also be used to define a distance from the plane Y that would be equivalent to the depth of the cup 80. Regardless, the plane Y and the vector X are generally used to determine a position of the cup 80 relative to the tracking sensor 58 for navigation of the instrument 52 and the cup 80 relative to the patient 14. Therefore, the vector X may be any appropriate vector and it is merely used to determine the orientation of the cup 80 relative to the patient 14.

Nevertheless, if the additional point determined in block 186 substantially defines an apex or top of the cup 80, the additional point determined in block 186 may be used to define a depth of the cup 80. Alternatively, or additionally, a known depth of the cup 80 may be entered into the tracking system 44 such that the tracking system 44 is programmed or has entered into it the depth of the cup 80. Therefore, the depth of the cup need not be determined with the point in block 186 but is known and entered into the tracking system 44 or may be stored in the system and recalled by a user or automatically by the tracking system 44.

Further, any appropriate member may be then be interchanged with the cup 80 on the instrument 50. Because the plane Y defines a plane of the rim 81, any other cup, reamer, or other appropriate member that is equivalent to the cup 80, may be positioned on the instrument 52 after the plane Y has been determined. The additional or alternative cups may include a different diameter but a substantially equivalent depth such that the plane Y determined in block 168 may also define a plane of a larger diameter cup due to the fact that the rim of the additional cup is positioned in a substantially similar spot as the rim 81 of the cup 80. If the cup 80 is changed or a different member, such as the reamer, is attached to the instrument simply determining or entering into the tracking system 44 a dimension of the changed cup may allow the tracking system 44 to determine a position of the plane Y and the vector X by doing a transformation calculation. Various changes may be made for procedures such as trialing various cups or gradually increasing the size of a reamer.

Once the plane Y and the vector X is determined with the first attachment member the tracking system 44 may automatically transform the position of the plane Y and the vector X depending upon a changed attachment member. The transformation, for example, may include moving the defined plane 1 mm closer to the tracking sensor 58 along the axis 98*a*. Regardless of the transformation performed it will be understood that the physical calibration process may be performed, once and may then be used to calibrate any subsequent attachment member.

The various other attachment members may include cups 80 of various sizes. As discussed above the plurality of cups 80 may be provided in a kit of varying depths. Once the first cup 80 has been calibrated the remaining cups need not be recalibrated according to the method 130, but may use the defined plane Y and vector X that are transformed by the tracking system according to appropriate algorithms or methods. For example, the various cups 80 may be provided in a look-up table and the user selects the attached cup and the tracking system may appropriately transform the determined plane Y and vector X.

Further, the additional points touched in block 182 may be transformed to define a three dimension cup, when the cup is generally symmetrical. A cup including a large diameter would merely have the point moved out on a radius from a center of the cup the increased distance or the differential in the radius of the cup that is changed. Therefore, once the plane Y is defined relative to the tracking sensor 58, the cup may be changed for any appropriate purposes, such as trialing an implantation, selecting a different size cup, or the like. Regardless, a determination of the plane need not occur again after determining the plane Y.

The method 130 in conjunction with the method 160 or any appropriate combination can be used to digitize at least a portion of the cup 80 or any appropriate attachment member relative to the instrument 50. Further, the instrument 52 can be in any appropriate orientation, such as having the offset shaft 90, a straight shaft or any other orientation. The plane Y is created by digitizing various points on the attachment member, such as the cup 80, rather than relying on a pre-known or known orientation of the cup relative to the instrument 52. Therefore, the instrument 52 can be used with any appropriate attachment member, such as the cup 80, without previously knowing a size, orientation, geometry, or the like of the instrument 52. Rather, the tracking sensor 58, being attached to the instrument 52 in a fixed position, can be used to register or calibrate the position of the cup 80 relative to the tracking sensor 58 for use in a navigation procedure. Further, any attachment member, other than the cup 80, may be digitized into the system 10 using the determination techniques.

Further, various other geometries of the cup 80 may be determined. For example, the probe 66 may be used to trace a surface of the cup 80 such that the entire geometry of the cup 80 can be known by the navigation system 80 and may be digitized for display on the display 36. For example, a plurality of longitudes may be traced with the probe 66 and the tracking system 44 including the workstation 34, may determine a shape and size of the cup 80 for display.

Further, a single line may be drawn on the surface of the cup 80 and the workstation may extrapolate the entire geometry of the cup 80. For example, if the cup 80 is generally symmetrical such that a single line drawn from an apex of the cup 80 to the rim 81 of the cup 80, the line may be rotated, either in real space or computer space, to create an entire surface of the dome of the cup 80 for display on the display 36. That is, the line may be drawn from the center point to the rim 81 of the cup and the center point may be used to determine a central axis of the cup 80 so that rotation around the axis through the center point of the line defining a lie on the dome of the cup 80, will substantially define a three dimensional shape of the cup 80. The rotation of the cup 80 may be either real or virtual.

Determining the three-dimensional shape and dimensions of the cup 80, in addition to the methods described above, may also include preacquired or stored dimensions of the cup 80. For example, the cup 80 may be known to have a selected depth, diameter, thickness and the like. The known dimensions of the cup 80 may be stored in memory system accessible by a processor, such as the one in the workstation 34. Therefore, a user may determine the plane and vector according to the methods described above or any appropriate method, and then select from the memory system the particular cup attached to the instrument 52. Therefore, the processor having access to the stored dimensions of the cup 80 may then illustrate the dimensions of the cup 80 relative to the patient 14 on the display 36 in the form of an icon or graphical rendering.

Also, the instrument 52 may be calibrated relative to the tracking sensor 58 affixed to the instrument 52. For example, the distal portion of the engagement end 86 may be touched with a probe 66 and the point determined relative to the tracking sensor 58 in a method similar to that described above. Therefore, a determination of the distal end of the instrument 52 may be known relative to the tracking sensor 58. The tracking system 44 may use this information in conjunction with the known or determined information of the cup 80 to determine a position of the cup 80 relative to the patient 14 during the navigation of the cup 80 for implantation.

Although the method 130 may be used with any appropriate cup, various cups may include selected points to be touched by the probe 66 for various purposes. For example, the cup 80 may include divots or marked spots that can be used for precise determination of a particular cup. For example, a cup may include a divot that, when used in the navigation system, allows for the processor to automatically determine the type of cup, including its dimension, size, and the like, from a look-up table stored in the memory system. Further, various portions on the cup may be chosen to be determined for navigation of the system. For example, various screw holes, fixation spikes, high points and the like may be determined with the navigation system 10 to assist in positioning and implanting the cup 80.

Further, with reference to various other portions such as the reamer 82, it may be desirable to pass the reamer 82 through the patient 14 and adjacent various soft tissues portions in a selected manner. Therefore, various regions of the cup may be selected or digitized by touching them with the probe 66 so that while passing the reamer portion 82 through the soft tissue, the reamer 82 may be oriented in a selected position to assist in assuring the appropriate orientation of the reamer 82 relative to the soft tissues.

Further, as discussed above, the plane Y may be substantially similar for each of the cups that may be positioned on the instrument 52. Therefore, the work station 34 may be used to transform the dimensions of the cup 80 or any cup selectively affixed to the instrument 52 while maintaining or using the plane Y for determining a position of the cup 80 relative to the instrument 52. Therefore, procedures may be performed more efficiently by quickly allowing the computer to alter the acquired or known dimensions without specifically requiring various points defined by the surface of the cup 80. This is assisted in that the tracking sensor 58 is not moved once the calibration begins and the plane Y is determined.

Figure 7A:
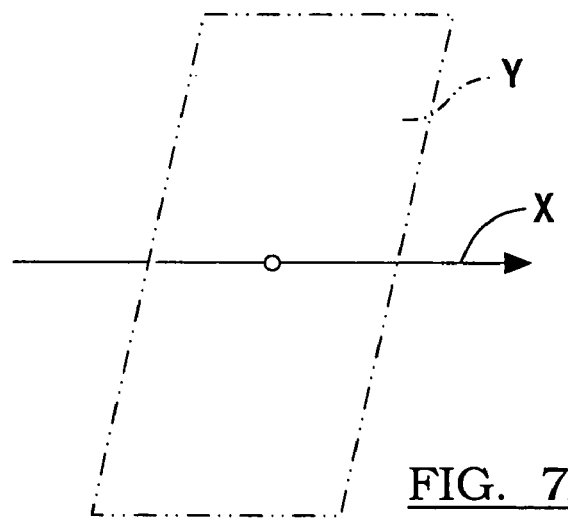
FIGS. 7A-7C are perspective views of various images, icons, and information that may be displayed.
Figure 7B:
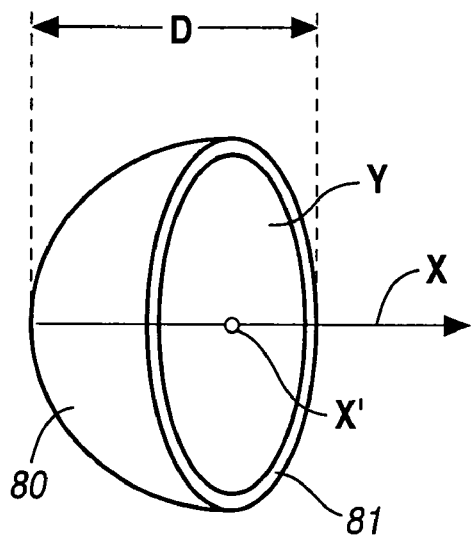
Figure 7C:
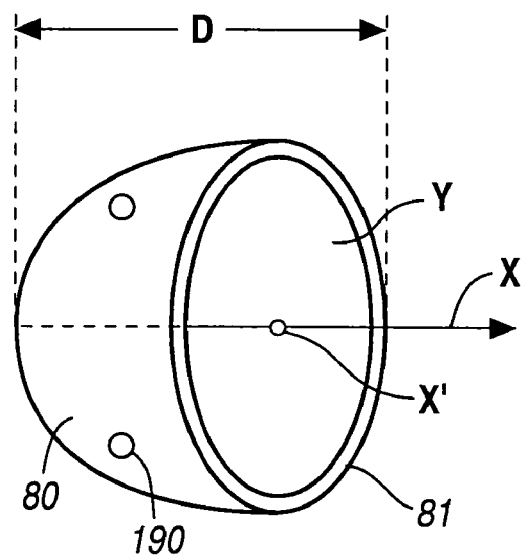

With reference to FIGS. 7A-7C, various amounts of information may be determined or illustrated on the display 36 according to the method employed. For example, with reference to FIG. 7A, using the method illustrated in method 130 and 160, the plane Y may be determined relative to the vector X and the information of vector X relative to any appropriate portion may be used for navigating the implant, such as the cup 80 or the reamer, or any appropriate member relative to the patient 14. Various other pieces of information, however, may not be displayed or required such as a specific depth or diameter of the cup or reamer. Although the depth of the cup or reamer may be determined, the information regarding the surface defined by the plane Y and the vector X may be the only information to perform the navigation of the portion relative to the patient 14. The plane Y and the vector X may be displayed as icons on the display 36 for viewing by a user. The icons may be superimposed over the images of the patient for navigation of the cup 80.

With reference to FIG. 7B, however, the distance or depth D which may define a depth of the implant 80 may also be determined. The depth D may be used to illustrate or represent the implant 80 on the display 36 or may simply be defined as a point showing a final depth or a depth of the implant 80. Further, the plane Y may merely be defined as a surface defined as the rim 81 of the cup 80. Further, the vector X may be determined as extending from the point X1, which can be the apex of the cup 80, and through the plane Y at a point X'. This allows for a determination of the depth of the cup 80 for determining an appropriate position of the cup 80 or an appropriate reamer depth. It will also be understood that the depth D may be determined from pre-acquired or stored dimensions of the cup 80 from known or selected cups or other parts, such as the reamer 82, for the procedure. All of this information may also be displayed on the display 36. Icons may be produced representing the plane Y, vector X, and the apex or depth D that may be superimposed over the images of the patient. This may assist a user in navigating the cup 80.

With reference to FIG. 7C, a graphical representation of the cup 80 may be illustrated in addition to the vector X that passes through the plane Y at point X'. Further, the depth D may also be shown on the display 36 by either determining the apex of the implant 80 or determining the appropriate implant 80 for display on the display 36. Further, other portions, such a screw hole 190 may be displayed on the display 36 by registering or calibrating the position of the screw hole 190 of the cup 80 for display on the display 36. As discussed above, the screw hole 190 may be determined by using the probe 66 to touch the screw hole 190 or a known orientation of the implant 80 relative to the instrument 52 and knowing the specifics of the dimensions of the implant 80 may also be used to determine the position of the screw hole 190. The rendering of the cup 80, including various portions such as the holes 190 may also be superimposed on the images of the patient on the display 36. The rendered image may be used to assist in navigating the cup 80.

Therefore, the methods according to various embodiments may be used to determine various amounts of information regarding the implant 80 and its navigation relative to the patient 14 for various purposes. For example, a procedure may be performed in determining only the plane Y and the vector X while other uses or users may desire to have a complete rendering or representation of the implant 80.

Various other methods may be used to determine various types of information regarding the implant, such as the cup 80. For example, in addition to or in the alternative to touching various points on the cup 80 after it has been attached to the instrument 52, the cup 80 may be digitized using various imaging techniques. For example, the cup 80 may be affixed to the instrument 52 including the tracking sensor 58. With reference to FIG. 4, at least images along two different axes may be acquired of the implant 80 affixed to the instrument 52. The images acquired of the implant 80 may be substantially two dimensional images that may be acquired using various imaging techniques such as digital photography and the like. The processor, such as the one in the workstation 34, may transform the two dimensional images taken along the two axes, or at least two axes of the implant 80, into a substantially three dimensional (3D) digitized image. The 3D digitized image may then be used to determine the plane Y and the vector X.

The transformation of the 2D images to 3D images or image data are generally known in the art and not described in detail herein. However, the tracking system 44 may use the digitized image for display on the display 36 and for determining the various information, such as the plane Y and the vector X. This information relative to the tracking sensor 58 may be used to determine the position of the implant 80 as it is being moved with the instrument 52 to navigate the procedure. Further, the digitized image may be confirmed based upon stored or known dimensions, orientations, and the like of the cup 80. The known dimensions may be used to confirm the digitized image for use in the procedure. Also a user may use an input device, such as a mouse, to determine points on the digitized image to define the pane Y and the vector X.

Further, various techniques may be used to determine points on the surface of the dome of the cup 80. For example, screw-holes, fixation points, edges of the rim 81 and the like may be determined using the various edge recognition techniques.

Therefore, it will be understood that the digitization, including various amounts of information, may be determined using various techniques so that the instrument 52 may be provided in any appropriate orientation, such as one that is straight or non-linear, for various purposes. The navigation system alone may be used with the instrument, such as probe 66, to determine various points to define a plane and vector of the cup 80. Various techniques may be employed, such as tracing the cup, image transformation techniques, and the like may be use used to digitize an image of the cup 80 for display on the display 36. Regardless, the various methods that may be used to determine orientation and position of the cup 80 on the instrument 52. The determined information, such as the plane Y and the vector X may be used while tracking the instrument 52 to navigate the cup 80.

Further, it will be understood that the use of the cup 80 is merely exemplary and the reamer 82 may also be used. For example, the reamer 82 may be affixed to the instrument 52 and the technique similar to that used to determine a position cup may be used to calibrate a position of the reamer 82 relative to the tracking sensor 58. The instrument 52 may then be tracked and the reamer 82 may be navigated relative to the patient 14. Further, various other implants may also be calibrated to the instrument 52 and navigated in a similar manner. For example, a hip stem implant may be affixed to the instrument 52 and various portions of the implant, such as an exterior surface, an axis, a position of various portions, and the like may be determined to assist in navigation of the implant relative to the patient 14. Further, the navigation techniques and the determination of various parts, such as the plane Y and the axis X may be used to navigate the various parts, such as the cup 80, when the cup 80 cannot be viewed by the user.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A system to navigate an instrument relative to a portion of a patient's anatomy, comprising:
   an instrument including an engaging end, a working end, and a non-linear shaft extending between said engaging end and said working end;
   a member selectively engageable to said engaging end such that said member is operable to be engaged and disengaged from said engaging end;
   a first tracking sensor interconnected with said instrument at said working end of said shaft; and
   a tracking system configured to track said first tracking sensor;
   wherein said tracking system comprises a processor configured to determine an orientation of said member relative to said first tracking sensor when said member is engaged to said engaging end by:
      determining at least three points on a portion of said member;
      determining a plane of the first member based at least in part upon the determined three points;
         confirming the accuracy of the determined plane by:
            determining a fourth point on the portion of the first member that should be on the determined plane; and
            determining whether the fourth point is on the determined plane;
   wherein said engaging end defines a first axis that is non-coaxial with a second axis defined by said working end such that said first tracking sensor is connected to the working end of the shaft that is non-coaxial and non-linear with said engaging end.

2. The system of claim 1, further comprising:
a probe having a second tracking sensor;
wherein said first tracking sensor and said second tracking sensor can be tracked relative to one another.

3. The system of claim 2, wherein at least one of said first tracking sensor or said second tracking sensor is selected from the group consisting of an optical sensor, an electromagnetic sensor, an acoustic sensor, a radiation sensor, gravimetric sensor, and combinations thereof.

4. The system of claim 2, wherein said member defines a portion operable to be selectively touched with said probe to determine a point in image space relative to said first tracking sensor of said portion.

5. The system of claim 1, further comprising:
an imaging system operable to obtain image data of the patient; and
a display to display an image of the patient based upon the image data and a rendering of the member.

6. The system of claim 1, wherein said instrument is selected from the group consisting of an impactor, a driver, an inserter, a handle, and combinations thereof.

7. The system of claim 1, wherein said member is selected from the group consisting of an implant, a tool, a rasp, a reamer, a drill, an acetabular implant, an acetabular reamer, a femoral implant, a femoral rasp, a tibial implant, a humeral head implant, a glenoid reamer, and combinations thereof.

8. The system of claim 1, wherein said member includes an acetabular implant operable to be positioned into an acetabulum of the patient's anatomy.

9. The system of claim 1, wherein said member includes a reamer operable to interconnect with said instrument to ream an acetabulum of the patient's anatomy.

10. The system of claim 1, wherein said member includes an attachment member having a unique dimension, wherein the unique dimension is stored in a memory system accessible by a processor.

11. The system of claim 1, wherein said first tracking sensor is integral with said instrument.

12. The system of claim 1, wherein said tracking system is operable to determine at least a portion of a geometry defined by said member including a plane defined by said member.

13. The system of claim 12, wherein said member is an acetabular implant and said plane is defined by a rim of said acetabular implant.

14. The system of claim 1, wherein said member has a geometry defined by a vector extending through a plane defined by said member.

15. The system of claim 14, wherein said tracking system is operable to determine an angle between said vector and said patient.

16. The system of claim 14, wherein said vector originates at a point substantially at an apex of the member wherein a distance between the point and the plane define a depth of said member.

17. The system of claim 1, wherein said member includes an attachment member including a unique dimension.

18. The system of claim 17, wherein said attachment member includes at least one of an acetabular implant or reamer each including a unique depth.

19. The system of claim 1, wherein said member includes indicia.

20. The system of claim 1, wherein said first tracking sensor is removeably coupled to said instrument.

21. A method of determining a position of a first member relative to an instrument, comprising:
interconnecting a first tracking sensor with the instrument;
interconnecting the first member with the instrument;
determining at least three points on a portion of said member;
determining a plane of the first member based at least in part upon the determined three points;
confirming the accuracy of the determined plane by:
determining a fourth point on the portion of the first member that should be on the determined plane; and
determining whether the fourth point is on the determined plane; and
determining a vector of the first member through the plane.

22. The method of claim 21, further comprising:
tracking a second tracking sensor interconnected with a probe relative to the first member after the first member is interconnected with the instrument.

23. The method of claim 22, wherein at least one of said first tracking sensor and said second tracking sensor is selected from the group consisting of an acoustic tracking sensor, an electromagnetic tracking sensor, a radiation tracking sensor, an optical tracking sensor, a gravimetric sensor, and combinations thereof.

24. The method of claim 22, wherein tracking a second tracking sensor includes touching at least three points on said first member with the probe and wherein determining a plane of the first member includes determining a plane defined by the three points.

25. The method of claim 24, wherein determining a vector includes touching a vector point on the first member and defining a vector originating at the vector point through the determined plane.

26. The method of claim 22, wherein tracking a second tracking sensor relative to the first tracking sensor includes tracing at least a portion of the first member with the probe to define a surface of the first member.

27. The method of claim 22, wherein the probe is touched to indicia on the member.

28. The method of claim 21, further comprising: selecting the instrument to include a substantially non-linear portion.

29. The method of claim 28, wherein interconnecting a first tracking sensor with the instrument includes positioning the first tracking sensor at a first end of the instrument that is interconnected with a second end of the instrument by the non-linear portion.

30. The method of claim 29, wherein interconnecting the first member and the instrument includes interconnecting the first member near the second end of the instrument;
wherein the first tracking sensor is connected to a portion of the instrument that is non-linear with the second end.

31. The method of claim 21, further comprising:
navigating the determined plane and the determined vector relative to a portion of a patient's anatomy for moving the first member relative to the patient's anatomy.

32. The method of claim 31, further comprising:
superimposing an icon representing at least the plane or the vector on an image of the patient.

33. The method of claim 31, further comprising:
superimposing a three dimensional graphical rendering of the member on an image of the patient.

34. The method of claim 21, further comprising:
selecting the first member to interconnect with the instrument, wherein the first member is a reamer, an acetabular implant, a femoral implant, a tibial implant, an orthopedic implant, or a tool.

35. The method of claim 21, wherein at least one of determining a plane or determining a vector is performed by a processor.

36. The method of claim 35, further comprising:
providing a memory system accessible by said processor;
wherein said memory system includes a lookup table including data regarding a plurality of the members.

37. The method of claim 36, wherein said plurality of members includes a plurality of unique dimensions stored in the lookup table.

38. The method of claim 21, wherein determining at least three points includes determining at least three points substantially equal distance apart to define the plane.

39. The method of claim 21, further comprising:
selecting a second member;
interconnecting the second member with the instrument after removing the first member from the instrument; and
transforming at least one of the plane and the vector based upon a different dimension of said second member.

40. The method of claim 39, further comprising:
providing a lookup table of the dimensions of the first member and the second member;
wherein transforming at least one of the vector on the plane is based upon the dimensions stored in the lookup table.

41. The method of claim 21, wherein if the fourth point is determined to not be on the determined plane determining at least three additional points.

42. The method of claim 21, further comprising:
touching a probe including a second tracking sensor to each of the three points and the fourth point.

43. A method of navigating a member relative to an anatomy of a patient, comprising:
interconnecting a first tracking sensor with an instrument;
interconnecting a member with the instrument;
tracking a probe to determine at least three points defined by the member to define a plane;
confirming the accuracy of the defined plane by tracking a probe to determine a fourth point on the member that should be on the defined plane and determining whether the fourth point is on the defined plane;
tracking a probe to determine a fifth point to define a vector through the plane relative to the member;
displaying the plane and the vector; and
navigating the member relative to the anatomy based at least in part on the displayed plane and vector.

44. The method of claim 43, further comprising:
selecting the instrument to include a substantially non-linear portion extending between a first end and a second end.

45. The method of claim 44, wherein said instrument includes a first end that is substantially non-coaxial with a second end.

46. The method of claim 44, wherein interconnecting the first tracking sensor includes interconnecting the first tracking sensor with the first end or the second end of the instrument.

47. The method of claim 44, wherein interconnecting the member with the instrument includes interconnecting the member with the other of the first end or second end of the instrument.

48. The method of claim 43, wherein tracking a probe to determine at least three points defined by the member includes touching the probe to at least three distinct points defined by the member.

49. The method of claim 48, wherein the points tracked are present on a rim of a member selected from the group consisting of an acetabular implant, a reamer, a femoral implant, a femoral rasp, and a tibial implant.

50. The method of claim 43, wherein tracking a second tracking sensor relative to the first tracking sensor includes tracking with a tracking system.

51. The method of claim 45, further comprising:
collecting image data of the anatomy of the patient with an imaging system;
displaying an image based upon the image data collected;
wherein navigating the member relative to the anatomy includes displaying an icon of the member relative to the image displayed.

52. The method of claim 51, wherein displaying the member includes displaying a three dimensional representation of the member relative to the image.

53. The method of claim 43, further comprising:
tracking the probe to determine a plurality of points to define a three dimensional shape of the member; and
displaying the three dimensional shape of the member on a display relative to image data of the patient.

54. The method of claim 43, further comprising:
providing a plurality of members each including a unique dimension; and
transforming the defined plane and the defined vector of the member based upon the unique dimension of each of the plurality of the members.

55. The method of claim 54, further comprising:
displaying the plane and the vector transformed based upon the unique dimensions of one of the plurality of members interconnected with the instrument.

56. The method of claim 43, wherein if the fourth point is determined to not be on the determined plane determining at least three additional points.

57. The method of claim 43, further comprising:
touching a probe including a second tracking sensor to each of the three points and the fourth point.

58. The method of claim 43, wherein the probe is touched to indicia on the member.

59. A method of determining a position of a first member relative to a first tracking sensor on an instrument, comprising:
interconnecting the first tracking sensor with the instrument;
interconnecting the first member with the instrument;
obtaining a two dimensional image data of the first member along at least two axes of the first member;
transforming the two dimensional data into a three dimensional geometry data of the first member with a processor;
determining a plane of the first member and determining a vector of the first member from the three dimensional transformation geometry data;
confirming accuracy of the determined plane by:
determining a point on the portion of said first member that should be on the determined plane; and
determining whether the point is on the determined plane; and
determining a position of the first member relative to the first tracking sensor on the instrument.

60. The method of claim 59, further comprising:
locating at least three points on a portion of said first member;
determining the plane of the first member based at least in part upon the located three points; and
determining the vector relative to the plane from a point on the first member.

* * * * *

UNITED STATES PATENT AND TRADEMARK OFFICE
CERTIFICATE OF CORRECTION

PATENT NO. : 7,636,595 B2  Page 1 of 1
APPLICATION NO. : 10/976328
DATED : December 22, 2009
INVENTOR(S) : Marquart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 837 days.

Signed and Sealed this

Ninth Day of November, 2010

David J. Kappos
*Director of the United States Patent and Trademark Office*